US010619096B2

(12) United States Patent
Park et al.

(10) Patent No.: US 10,619,096 B2
(45) Date of Patent: Apr. 14, 2020

(54) POPULATION OF QUANTUM DOTS AND A COMPOSITION INCLUDING THE SAME

(71) Applicant: SAMSUNG ELECTRONICS CO., LTD., Suwon-si, Gyeonggi-do (KR)

(72) Inventors: Garam Park, Seoul (KR); Tae Gon Kim, Hwaseong-si (KR); Nayoun Won, Suwon-si (KR); Shin Ae Jun, Seongnam-si (KR); Soo Kyung Kwon, Suwon-si (KR); Seon-Yeong Kim, Suwon-si (KR); Shang Hyeun Park, Yongin-si (KR); Jooyeon Ahn, Suwon-si (KR); Yuho Won, Seoul (KR); Eun Joo Jang, Suwon-si (KR); Hyo Sook Jang, Suwon-si (KR)

(73) Assignees: SAMSUNG ELECTRONICS CO., LTD., Gyeonggi-Do (KR); SAMSUNG DISPLAY CO., LTD., Gyeonggi-Do (KR); SAMSUNG SDI CO., LTD., Gyeonggi-Do (KR)

( * ) Notice: Subject to any disclaimer, the term of this patent is extended or adjusted under 35 U.S.C. 154(b) by 0 days.

(21) Appl. No.: 16/245,594

(22) Filed: Jan. 11, 2019

(65) Prior Publication Data

US 2019/0211265 A1 Jul. 11, 2019

(30) Foreign Application Priority Data

Jan. 11, 2018 (KR) ........................ 10-2018-0003831

(51) Int. Cl.
*H01L 21/00* (2006.01)
*C09K 11/88* (2006.01)
(Continued)

(52) U.S. Cl.
CPC .......... *C09K 11/883* (2013.01); *C09K 11/025* (2013.01); *C09K 11/565* (2013.01);
(Continued)

(58) Field of Classification Search
CPC ..... C09K 11/025; C09K 11/88; C09K 11/883; H01L 21/02601; H01L 27/322
See application file for complete search history.

(56) References Cited

U.S. PATENT DOCUMENTS

| 7,329,369 B2 | 2/2008 | Sato et al. |
|---|---|---|
| 7,378,151 B2 | 5/2008 | Sato et al. |

(Continued)

FOREIGN PATENT DOCUMENTS

| EP | 2853578 A1 | 4/2015 |
|---|---|---|
| EP | 3184603 A1 | 6/2017 |

(Continued)

OTHER PUBLICATIONS

Jian Cui et al., "Direct probe of spectral inhomogeneity reveals synthetic tunability of single-nanocrystal spectral linewidths", Nature Chemistry, Jun. 2, 2013, Paged 602-606, vol. 5.

(Continued)

*Primary Examiner* — Nicholas J Tobergte
(74) *Attorney, Agent, or Firm* — Cantor Colburn LLP

(57) ABSTRACT

Disclosed are a quantum dot population including a plurality of cadmium free quantum dots, a quantum dot polymer composite including the same, and a display device including the same. The plurality of cadmium free quantum dots includes: a semiconductor nanocrystal core comprising indium and phosphorous, a first semiconductor nanocrystal shell disposed on the semiconductor nanocrystal core and comprising zinc and selenium, and a second semiconductor nanocrystal shell disposed on the first semiconductor nanocrystal shell and comprising zinc and sulfur, wherein an average particle size of the plurality of cadmium free quantum dots is greater than or equal to about 5.5 nm, a standard deviation of particle sizes of the plurality of cadmium free quantum dots is less than or equal to about 20% of the average particle size, and an average solidity of the plurality (Continued)

of cadmium free quantum dots is greater than or equal to about 0.85.

27 Claims, 13 Drawing Sheets

(51) Int. Cl.

| | | |
|---|---|---|
| *C09K 11/02* | (2006.01) | |
| *H01L 27/32* | (2006.01) | |
| *F21V 8/00* | (2006.01) | |
| *G02F 1/1335* | (2006.01) | |
| *G02F 1/13357* | (2006.01) | |
| *C09K 11/70* | (2006.01) | |
| *C09K 11/56* | (2006.01) | |
| *H05B 33/14* | (2006.01) | |
| *B82Y 20/00* | (2011.01) | |
| *B82Y 40/00* | (2011.01) | |

(52) U.S. Cl.
CPC .............. *C09K 11/70* (2013.01); *G02B 6/005* (2013.01); *G02F 1/133514* (2013.01); *G02F 1/133617* (2013.01); *H01L 27/322* (2013.01); *H05B 33/14* (2013.01); *B82Y 20/00* (2013.01); *B82Y 40/00* (2013.01); *G02F 2001/133614* (2013.01); *G02F 2202/36* (2013.01)

(56) References Cited

U.S. PATENT DOCUMENTS

| | | | |
|---|---|---|---|
| 9,133,394 B2 | 9/2015 | Freeman et al. | |
| 9,138,711 B2 | 9/2015 | Treadway et al. | |
| 9,260,655 B2 | 2/2016 | Freeman et al. | |
| 9,334,440 B2 | 5/2016 | Jang et al. | |
| 10,074,770 B2 * | 9/2018 | Park ...................... | H01L 33/04 |
| 2010/0276638 A1 | 11/2010 | Liu et al. | |
| 2014/0001405 A1 | 1/2014 | Guo et al. | |
| 2017/0183565 A1 * | 6/2017 | Jun ...................... | C09K 11/025 |
| 2017/0250322 A1 | 8/2017 | Wang et al. | |
| 2017/0306227 A1 * | 10/2017 | Ippen .................... | C09K 11/70 |
| 2017/0335187 A1 * | 11/2017 | Guo ...................... | C09K 11/883 |
| 2018/0033856 A1 * | 2/2018 | Kwon .................... | C09K 11/70 |
| 2019/0006556 A1 * | 1/2019 | Park ...................... | H01L 33/04 |
| 2019/0211261 A1 * | 7/2019 | Jang ...................... | H01L 27/322 |

FOREIGN PATENT DOCUMENTS

| | | |
|---|---|---|
| JP | 2004243507 A | 9/2004 |
| JP | 2006213592 A | 8/2006 |
| KR | 20110069836 A | 6/2011 |
| KR | 20110091691 A | 8/2011 |
| KR | 20140075038 A | 6/2014 |
| KR | 20150126958 A | 11/2015 |
| KR | 20150128988 A | 11/2015 |
| KR | 20170075874 A | 7/2017 |
| WO | 2010040100 A2 | 4/2010 |
| WO | 2012035535 A1 | 3/2012 |
| WO | 2015094646 A1 | 6/2015 |
| WO | 2017096229 A1 | 6/2017 |

OTHER PUBLICATIONS

Extended European Search Report dated May 20, 2019, of the corresponding European Patent Application No. 19000018.2.

* cited by examiner

POPULATION OF QUANTUM DOTS AND A COMPOSITION INCLUDING THE SAME

CROSS-REFERENCE TO RELATED APPLICATION

This application claims priority to Korean Patent Application No. 10-2018-0003831, filed in the Korean Intellectual Property Office on Jan. 11, 2018, and all the benefits accruing therefrom under 35 U.S.C. § 119, the content of which is incorporated herein in its entirety by reference.

BACKGROUND

1. Field

A population of quantum dots, a composition or composite including same, and an electronic device including the same are disclosed.

2. Description of the Related Art

Quantum dots (e.g., nano-sized semiconductor nanocrystals) having different energy bandgaps may be obtained by controlling their sizes and compositions. Quantum dots may exhibit electroluminescent and photoluminescent properties. In a colloidal synthesis, organic materials such as a dispersing agent may coordinate, e.g., be bound, to a surface of the semiconductor nanocrystal during the crystal growth thereof, thereby providing a quantum dot having a controlled size and having luminescent properties. From an environmental standpoint, developing a cadmium free quantum dot with improved luminescent properties is desirable.

SUMMARY

An embodiment provides a population of cadmium free quantum dots that may exhibit improved photoluminescence properties (e.g., enhanced excitation light absorption rate) and enhanced stability.

Another embodiment provides a method of producing the population of the cadmium free quantum dots.

Yet another embodiment provides a composition including the population of cadmium free quantum dot.

Still another embodiment provides a quantum dot-polymer composite including the population of cadmium free quantum dot.

Further another embodiment provides an electronic device including the quantum dot-polymer composite.

In an embodiment, a population of quantum dot includes a plurality of cadmium free quantum dots, wherein the plurality of cadmium free quantum dots include a semiconductor nanocrystal core including indium (In) and phosphorous (P), a first semiconductor nanocrystal shell disposed on the semiconductor nanocrystal core and including zinc and selenium, and a second semiconductor nanocrystal shell disposed on the first semiconductor nanocrystal shell and including zinc and sulfur, wherein an average particle size of the plurality of cadmium free quantum dots is greater than or equal to about 5.5 nanometers, a standard deviation of particle sizes of the plurality of cadmium free quantum dots is less than or equal to about 20% of the average particle size, and an average solidity of the plurality of cadmium free quantum dots is greater than or equal to about 0.85.

The cadmium free quantum dots may include an organic ligand on a surface thereof and the organic ligand may include a carboxylic acid compound (e.g., monocarboxylic acid compound) and a primary amine compound (e.g., monoamine compound).

The carboxylic acid compound may have a C5 to C30 hydrocarbon group (e.g., a C5 to C30 aliphatic group), and a primary amine group of the primary amine compound may have a C5 to C30 hydrocarbon group (e.g., a C5 to C30 aliphatic group).

The primary amine group may have a C5 to C30 alkenyl group.

The cadmium free quantum dots in an embodiment may not include boron.

The semiconductor nanocrystal core may further include zinc.

The first semiconductor nanocrystal shell may be disposed directly on the surface of the semiconductor nanocrystal core.

The average particle size of the plurality of the cadmium free quantum dots may be greater than or equal to about 5.8 nanometers, for example, greater than or equal to about 6 nanometers.

The standard deviation of particle sizes of the plurality of cadmium free quantum dots may be less than or equal to about 18% of the average particle size.

The average solidity of the plurality of cadmium free quantum dots may be greater than or equal to about 0.90.

A maximum photoluminescence peak of the plurality of cadmium free quantum dots may have a full width at half maximum of less than or equal to about 40 nm.

A quantum efficiency of the plurality of cadmium free quantum dots may be greater than or equal to about 70%.

The first semiconductor nanocrystal shell may not include sulfur.

A thickness of the first semiconductor nanocrystal shell may be greater than or equal to about 3 monolayers.

A thickness of the first semiconductor nanocrystal shell may be less than or equal to about 10 monolayers.

The second semiconductor nanocrystal shell may be an outermost layer of the quantum dot.

The second semiconductor nanocrystal shell may be disposed directly on the first semiconductor nanocrystal shell.

The second semiconductor nanocrystal shell may include ZnSeS, ZnS, or a combination thereof.

A molar ratio of a sum of sulfur and selenium with respect to indium [(Se+S)/In] may be greater than or equal to about 10:1, for example, greater than or equal to about 11:1.

A molar ratio of a sum of sulfur and selenium with respect to indium (Se+S/In) may be less than or equal to about 40:1, for example, less than or equal to about 30:1.

The cadmium free quantum dots may have a molar ratio of selenium with respect to sulfur of greater than or equal to about 1:1, for example, greater than or equal to about 1.1:1. The cadmium free quantum dots may have a molar ratio of selenium with respect to sulfur of less than or equal to about 3:1, for example, less than or equal to about 2.8:1.

A sum of thicknesses of the first and second semiconductor nanocrystal shells may be greater than or equal to about 1.5 nm, for example, greater than or equal to about 2 nm.

In other embodiments, a method of producing the cadmium free quantum dot includes:

reacting a zinc containing precursor and a selenium containing precursor in the presence of a semiconductor nanocrystal core particle including indium and phosphorous in a heated organic solvent and an organic ligand at a first reaction temperature (e.g., for a time period of greater than or equal to about 40 minutes) to form a first semiconductor nanocrystal shell on the semiconductor nanocrystal core; and reacting a zinc containing precursor and a sulfur containing precursor in the presence of a particle having the first semiconductor nanocrystal shell formed on the core in the organic solvent and the organic ligand at a second reaction temperature to form a second semiconductor nanocrystal shell on the first semiconductor nanocrystal shell, wherein the organic ligand includes a carboxylic acid compound and a primary amine compound.

During the formation of the first semiconductor nanocrystal shell, the organic ligand may include the carboxylic acid compound and the primary amine compound.

The method may not include lowering a temperature of a reaction mixture including the particle having the first semiconductor nanocrystal shell on the core to a temperature below about 100° C., i.e., maintaining the temperature of the reaction mixture at a temperature of greater than or equal to about 100° C.

In another embodiment, a quantum dot polymer composite includes a polymer matrix; and a plurality of quantum dots dispersed in the polymer matrix, wherein the plurality of quantum dots includes the aforementioned population of the cadmium free quantum dots.

The polymer matrix may include a crosslinked polymer, a binder polymer having a carboxylic acid group, or a combination thereof.

The crosslinked polymer may include a polymerization product of a photopolymerizable monomer including at least carbon-carbon double bond, optionally a polymerization product of the photopolymerizable monomer and a multi-thiol compound having at least two thiol groups at its terminal end, or a combination thereof.

The plurality of the quantum dots may not include cadmium.

The quantum dot polymer composite may include a plurality of fine metal oxide fine particles in the polymer matrix.

A blue light absorption rate of the quantum dot polymer composite with respect to light having a wavelength of 450 nanometer may be greater than or equal to about 88% (for example when an amount of the cadmium free quantum dot is less than or equal to about 45% based on a total weight of the composite).

The quantum dot polymer composite may be configured to have a photoluminescent peak with a full width at half maximum of less than or equal to about 40 nm.

In another embodiment, a display device includes a light source and a light emitting element (e.g., photoluminescence element), wherein the light emitting element includes the aforementioned quantum dot-polymer composite and the light source is configured to provide the light emitting element with incident light.

The incident light may have a luminescence peak wavelength of about 440 nanometers to about 460 nanometers.

In an embodiment, the light emitting element may include a sheet including the quantum dot polymer composite.

The display device may further include a liquid crystal panel, and a sheet of the quantum dot polymer composite may be disposed between the light source and the liquid crystal panel.

In an embodiment, the display device includes as the light emitting element a stacked structure including a substrate and a light emitting layer disposed on the substrate, wherein the light emitting layer includes a pattern of the quantum dot polymer composite and the pattern includes at least one repeating section configured to emit light at a predetermined wavelength.

The display device (e.g., the light emitting element) may be configured to have a color reproducibility of greater than or equal to about 80% measured in accordance with a BT2020 standard.

The pattern may include a first section configured to emit first light and a second section configured to emit second light having a different center wavelength from the first light.

The light source may include a plurality of light-emitting units corresponding to each of the first section and the second section, wherein the light-emitting units may include a first electrode and a second electrode facing each other and an electroluminescence layer disposed between the first electrode and the second electrode.

The display device may further include a lower substrate, a polarizer disposed under the lower substrate, and a liquid crystal layer disposed between the stacked structure and the lower substrate, wherein the stacked structure is disposed so that the light emitting layer faces the liquid crystal layer.

The display device may further include a polarizer between the liquid crystal layer and the light emitting layer.

The light source may include an LED and optionally a light guide panel.

A population of cadmium free quantum dots of an embodiment may have increased solidity and improved size distribution. Thus, the population of cadmium free quantum dots of the embodiment may exhibit a decreased FWHM and a quantum dot polymer composite including the same may exhibit increased excitation light absorption rate and enhanced light conversion rate. The cadmium free quantum dot of the embodiments may be used in various display devices and biological labelling (e.g., bio sensor, bio imaging, etc.), a photo detector, a solar cell, a hybrid composite, and the like. A display device including the population of cadmium free quantum dots of the embodiment may exhibit improved display quality (e.g., increased color reproducibility under a next generation color standard, BT2020)

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
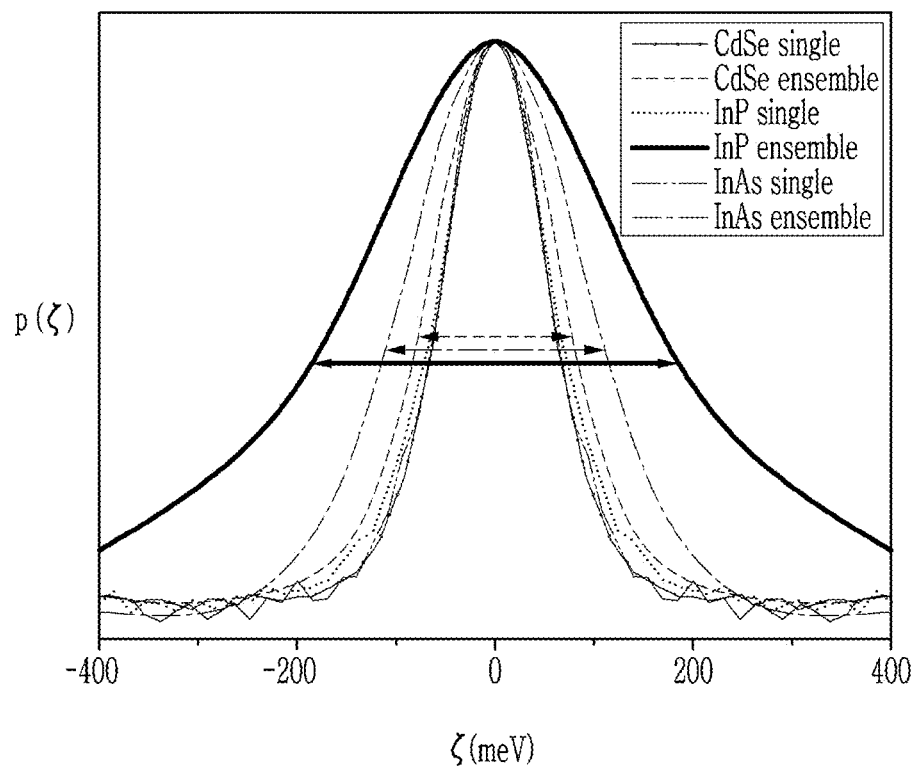
FIG. 1 is a view illustrating a photoluminescent peak and its full width at half maximum of a single core and an ensemble thereof for a cadmium based quantum dot and cadmium free quantum dots.

Advantages and characteristics of this disclosure, and a method for achieving the same, will become evident referring to the following example embodiments together with the drawings attached hereto. However, the embodiments should not be construed as being limited to the embodiments set forth herein. If not defined otherwise, all terms (including technical and scientific terms) in the specification may be defined as commonly understood by one skilled in the art. The terms defined in a generally-used dictionary may not be interpreted ideally or exaggeratedly unless clearly defined. In addition, unless explicitly described to the contrary, the word "comprise" and variations such as "comprises" or "comprising", will be understood to imply the inclusion of stated elements but not the exclusion of any other elements.

Further, the singular includes the plural unless mentioned otherwise.

In the drawings, the thickness of layers, films, panels, regions, etc., are exaggerated for clarity. Like reference numerals designate like elements throughout the specification.

It will be understood that when an element such as a layer, film, region, or substrate is referred to as being "on" another element, it can be directly on the other element or intervening elements may also be present. In contrast, when an element is referred to as being "directly on" another element, there are no intervening elements present.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±10% or 5% of the stated value.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

It will be understood that, although the terms "first," "second," "third" etc. may be used herein to describe various elements, components, regions, layers and/or sections, these elements, components, regions, layers and/or sections should not be limited by these terms. These terms are only used to distinguish one element, component, region, layer or section from another element, component, region, layer, or section. Thus, "a first element," "component," "region," "layer" or "section" discussed below could be termed a second element, component, region, layer or section without departing from the teachings herein.

Furthermore, relative terms, such as "lower" or "bottom" and "upper" or "top," may be used herein to describe one element's relationship to another element as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower," can therefore, encompasses both an orientation of "lower" and "upper," depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

As used herein, unless a definition is otherwise provided, the term "substituted" refers to a compound or a group or a moiety wherein at least one hydrogen atom thereof is substituted with a substituent. The substituent may include a C1 to C30 alkyl group, a C2 to C30 alkenyl group, a C2 to C30 alkynyl group, a C6 to C30 aryl group, a C7 to C30 alkylaryl group, a C1 to C30 alkoxy group, a C1 to C30 heteroalkyl group, a C3 to C30 heteroalkylaryl group, a C3 to C30 cycloalkyl group, a C3 to C15 cycloalkenyl group, a C6 to C30 cycloalkynyl group, a C2 to C30 heterocycloalkyl group, a halogen (—F, —Cl, —Br, or —I), a hydroxy group (—OH), a nitro group (—NO$_2$), a cyano group (—CN), an amino group (—NRR', wherein R and R' are the same or different, and are independently hydrogen or a C1 to C6 alkyl group), an azido group (—N$_3$), an amidino group (—C(=NH)NH$_2$), a hydrazino group (—NHNH$_2$), a hydrazono group (=N(NH$_2$)), a group represented by the formula =N—R (wherein R is hydrogen or a C1 to C10 linear or branched alkyl group), an aldehyde group (—C(=O)H), a carbamoyl group (—C(O)NH$_2$), a thiol group (—SH), an ester group (—C(=O)OR, wherein R is a C1 to C6 alkyl group or a C6 to C12 aryl group), a carboxylic acid group (—COOH) or a salt thereof (—C(=O)OM, wherein M is an organic or inorganic cation), a sulfonic acid group (—SO$_3$H) or a salt thereof (—SO$_3$M, wherein M is an organic or inorganic cation), a phosphoric acid group (—PO$_3$H$_2$) or a salt thereof (~PO$_3$MH or —PO$_3$M$_2$, wherein M is an organic or inorganic cation), or a combination thereof.

As used herein, unless a definition is otherwise provided, the term "hetero" means that the compound or group includes at least one (e.g., one to three) heteroatom(s), wherein the heteroatom(s) is each independently N, O, S, Si, P, or a combination thereof.

As used herein, unless a definition is otherwise provided, the term "alkylene group" refers to a straight or branched chain, saturated aliphatic hydrocarbon group having a valence of at least two. The alkylene group may be optionally substituted with one or more substituents.

As used herein, unless a definition is otherwise provided, the term "arylene group" refers to a functional group having a valence of at least two and formed by the removal of at least two hydrogen atoms from one or more rings of an aromatic hydrocarbon, wherein the hydrogen atoms may be removed from the same or different rings (preferably different rings), each of which rings may be aromatic or nonaromatic. The arylene group may be optionally substituted with one or more substituents.

As used herein, unless a definition is otherwise provided, the term "aliphatic hydrocarbon group" refers to a C1 to C30 linear or branched alkyl group, C2 to C30 linear or branched alkenyl group, and C2 to C30 linear or branched alkynyl group, the term "aromatic hydrocarbon group" refers to a C6 to C30 aryl group or a C2 to C30 heteroaryl group, and the term "alicyclic hydrocarbon group" refers to a C3 to C30 cycloalkyl group, a C3 to C30 cycloalkenyl group, and a C3 to C30 cycloalkynyl group.

As used herein, unless a definition is otherwise provided, the term "(meth)acrylate" refers to acrylate and/or methacrylate. The (meth)acrylate may include a (C1 to C10 alkyl)acrylate and/or a (C1 to C10 alkyl)methacrylate.

In some embodiment, "hydrophobic moiety" may be a moiety that may cause a compound including the same to agglomerate in an aqueous (hydrophilic) solution and to have a tendency to repel water. For example, the hydrophobic moiety may include an aliphatic hydrocarbon group (e.g., alkyl, alkenyl, alkynyl, etc.) having at least one (e.g., at least two, three, four, five, or six, or higher) carbon atoms, an aromatic hydrocarbon group having at least six carbon atoms (e.g., phenyl, naphthyl, arylalkyl group, etc.), or an alicyclic hydrocarbon group having at least five carbon atoms (e.g., cyclohexyl, norbornenyl, etc.).

As used herein, unless a definition is otherwise provided, the term "dispersion" refers to a system in which a dispersed phase is a solid and a continuous phase includes a liquid. For example, the term "dispersion" may refer to a colloidal dispersion, wherein the dispersed phase includes particles having a dimension of at least about 1 nanometer (nm) (e.g., at least about 2 nm, at least about 3 nm, or at least about 4 nm) and less than or equal to about several micrometers (μm) (e.g., 1 μm or less, 2 μm or less).

As used herein, the term "a population of quantum dot" and the term "quantum dot population" are interchangeable.

As used herein, unless a definition is otherwise provided, the term "Group" in the term Group III, Group II, and the like refers to a group of the Periodic Table of Elements.

As used herein, "Group I" refers to Group IA and Group IB, and may include Li, Na, K, Rb, and Cs but are not limited thereto.

As used herein, "Group II" refers to Group IIA and a Group IIB, and examples of the Group II metal may include Cd, Zn, Hg, and Mg, but are not limited thereto.

As used herein, "Group III" refers to Group IIIA and Group IIIB, and examples of the Group III metal may include Al, In, Ga, and Tl, but are not limited thereto.

As used herein, "Group IV" refers to Group IVA and Group IVB, and examples of the Group IV metal may include Si, Ge, and Sn but are not limited thereto. As used herein, the term "a metal" may include a semi-metal such as Si.

As used herein, "Group V" refers to Group VA and may include nitrogen, phosphorus, arsenic, antimony, and bismuth but is not limited thereto.

As used herein, "Group VI" refers to Group VIA and may include sulfur, selenium, and tellurium, but is not limited thereto.

A semiconductor nanocrystal particle (also referred to as a quantum dot) is a nano-sized crystalline material. The semiconductor nanocrystal particle may have a large surface area per unit volume due to its very small size and may exhibit different characteristics from bulk materials having the same composition due to a quantum confinement effect. Quantum dots may absorb light from an excitation source to be excited, and may emit energy corresponding to an energy bandgap of the quantum dots.

The quantum dots have a potential applicability in various devices (e.g., an electronic device) due to their unique photoluminescence characteristics. Quantum dots having properties currently applicable to an electronic device are mostly cadmium-based. However, cadmium may cause a serious environment/health problem and thus is a restricted element. As a type of cadmium free quantum dot, a Group III-V-based nanocrystal has been extensively researched. However, cadmium free quantum dots have technological drawbacks in comparison with the cadmium based ones.

For example, for their application in a device, quantum dots often use blue light (e.g., having a wavelength of about 450 nm) as excitation energy source. The cadmium based quantum dots generally have a high level of blue light absorption rate. However, in the case of currently available cadmium free quantum dots, the absorption strength for blue light (e.g., having a wavelength of about 450 nm) is not high, and this may lead to a decreased brightness. To be applicable to a device, quantum dots may be dispersed in a host matrix (e.g., including a polymer and/or inorganics) to form a composite. Such a quantum dot composite and/or a color filter including the same may provide a display that may show high brightness, wide viewing angle, and high color reproducibility. However, a weight of the quantum dots that may be included in the composite may be restricted due to various process-related problems. Thus, it is desirable to develop a cadmium free quantum dot having enhanced blue absorption rate and improved brightness at a given weight. It would be a further advantage if the quantum dot exhibited thermal stability.

Quantum dots based on a Group III-V compound including indium and phosphorous have a smaller energy bandgap and their Bohr radiuses are larger than those of the cadmium based quantum dots, which results in a greater change in a FWHM depending on their size. In the InP based quantum dots, the indium and the phosphorous have a high tendency to forming a covalent bond, which makes it difficult to form a uniform population of the nanoparticles in comparison with the cadmium based quantum dots, and thus has a substantial and adverse effect on the photoluminescent properties (e.g., the FWHM) of the resulting quantum dot. Referring to FIG. 1, in the case of the cadmium based quantum dot (e.g., a CdSe core), luminous properties of a single particle are not significantly different from those of ensembles (pluralities) thereof. In contrast, in the case of a quantum dot based on the indium phosphide (e.g., an InP core), properties of a single particle are significantly different from those of ensembles thereof. For example, in case of the InP core, a single particle exhibits a narrow FWHM while an ensemble thereof exhibits a greatly increased FWHM.

Moreover, a cadmium free quantum dot tends to have poor uniformity in a size of the core, and forming a shell (e.g., a ZnSe or ZnS shell) on the core may further aggravate its uniformity problem, such that non-uniformity may significantly increase. In order to enhance stability thereof, a ZnS shell may be provided as the outermost shell of the quantum dot, but a large difference in the lattice constant between the InP core and ZnS shell may make it more difficult to provide a uniform coating and thereby a core-shell type indium phosphide based quantum dot tends to have a wider particle size distribution. Therefore, in the case of the core-shell type quantum dot based on the indium phosphide prepared in a currently available method, a standard deviation of the particle size of the quantum dots is generally greater than 20% of the average particle size.

When the quantum dot has a thin shell, the uniformity of the particle size distribution may be controlled at a certain level. However, in case of the cadmium free quantum dot, a substantial increase in a shell thickness may be desired in order to secure quantum dot properties (e.g., quantum efficiency and stability). At the increased shell thickness, it is difficult for the quantum dots to have a desired level of uniformity in a particle size distribution and thus the standard deviation with respect to their average particle size tend to be greater than 20%.

In addition, the fact that a population of quantum dots has a wider particle size distribution and an increased FWHM may also suggest that the number of small particles not having a desired thickness of shell and the number of large particles having excessively increased thickness of shell may simultaneously increase. When such a population of quantum dots is processed into a composite, a desired level of stability cannot be assured and/or the number of the quantum dots per a given weight in the composite may decrease and thus desired optical properties (e.g., a blue light absorption rate and luminous efficiency) may not be obtained.

In an embodiment, a population of quantum dots includes a plurality of cadmium free quantum dots. The population of quantum dots may not include cadmium, i.e., may be free of cadmium or have no cadmium added. A cadmium free quantum dot (hereinafter, also referred to as "quantum dot") of an embodiment has a core-multishell structure. In the multi-shell structure, adjacent shells have different compositions from each other. The cadmium free quantum dots of an embodiment include a semiconductor nanocrystal core including indium and phosphorous, a first semiconductor nanocrystal shell disposed on the semiconductor nanocrystal core and including zinc and selenium, and a second semiconductor nanocrystal shell disposed on the first semiconductor nanocrystal shell and including zinc and sulfur, and not including cadmium. The first semiconductor nanocrystal shell may have a composition different from the second semiconductor nanocrystal shell.

An average particle size of the population of the cadmium free quantum dots of an embodiment may be greater than or equal to about 5.5 nm, for example, 5.6 nm or greater, greater than or equal to about 5.7 nm, greater than or equal to about 5.8 nm, greater than or equal to about 5.9 nm, greater than or equal to about 6.0 nm, greater than or equal to about 6.1 nm, greater than or equal to about 6.2 nm, greater than or equal to about 6.3 nm, greater than or equal to about 6.4 nm, greater than or equal to about 6.5 nm, greater than or equal to about 7.0 nm, greater than or equal to about 7.5 nm, greater than or equal to about 7.6 nm, greater than or equal to about 7.7 nm, greater than or equal to about 7.8 nm, greater than or equal to about 7.9 nm, or greater than or equal to about 8.0 nm. An average particle size of the population of the cadmium free quantum dots of an embodiment may be less than or equal to about 20 nm, for example, less than or equal to about 19 nm, less than or equal to about 18 nm, less than or equal to about 17 nm, less than or equal to about 16 nm, less than or equal to about 15 nm, less than or equal to about 14 nm, less than or equal to about 13 nm, less than or equal to about 12 nm, less than or equal to about 11 nm, less than or equal to about 10 nm, or less than or equal to about 9 nm. The particle size may be a diameter. (For example, when the particle is not substantially a sphere shape the particle size may be a diameter that is calculated by converting a two dimensional area determined in a transmission electron microscopic image into a circle).

A standard deviation of the particle sizes of the population of the cadmium free quantum dots may be less than or equal to about 20% of the average particle size. An average solidity of the population of the cadmium free quantum dots is greater than or equal to about 0.85.

Figure 2:
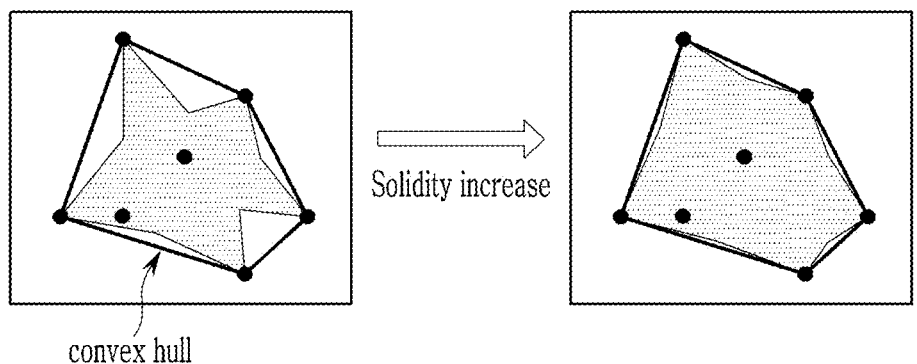
FIG. 2 is a view illustrating the concept of solidity of a particle.

As used herein, the term "solidity" refers to a ratio of an area (B) of a two dimensional area of a quantum dot with respect to an area A of a convex hull. The convex hull may be defined as the smallest convex set of points in which a set of all points constituting a two dimensional image of a given quantum dot obtained by an electron microscopic analysis is contained. (see FIG. 2) The solidity may be measured by a transmission electron scopic analysis. For example, a computer program (e.g., an image processing program such as "image J") may be used to calculate (an average value of) solidity from a TEM image of the quantum dots.

Efficient passivation of the core may require an increased thickness of coating, but the increase in the coating thickness may make the size distribution of the population of the particles wider and may cause a decrease in the solidity of each of the particles. Thus, when a population of indium phosphide based core-shell quantum dots is prepared in the conventional manner to have an average size of greater than or equal to about 5.5 nm (e.g., greater than or equal to about 5.6 nm), the size distribution has a standard deviation of greater than or equal to about 24% (e.g., greater than or equal to about 25%) and the average solidity thereof may be less than or equal to about 0.83 (e.g., less than or equal to about 0.80).

However, when being prepared in the method that will desired below, the population of the cadmium free quantum dots may have an average particle size of greater than or equal to about 5.5 nm, for example, greater than or equal to about 5.6 nm, greater than or equal to about 5.7 nm, greater than or equal to about 5.8 nm, greater than or equal to about 5.9 nm, or greater than or equal to about 6 nm and at the same time, a standard deviation of the population of the cadmium free quantum dots may be less than or equal to about 20%, for example, less than or equal to about 19%, less than or equal to about 18%, less than or equal to about 17%, less than or equal to about 16%, less than or equal to about 15%, or less than or equal to about 14% and an average solidity of the population of the cadmium free quantum dots may be greater than or equal to about 0.85, for example, greater than or equal to about 0.86, greater than or equal to about 0.87, greater than or equal to about 0.88, greater than or equal to about 0.89, or greater than or equal to about 0.9.

A population of the quantum dots having the aforementioned solidity and the particle size distribution may exhibit an improved level of a full width at half maximum. For example, a quantum dot population of an embodiment may have a FWHM of less than or equal to about 40 nm, for example, less than or equal to about 39 nm, less than or equal to about 38 nm, or less than or equal to about 37 nm.

In the cadmium free quantum dots, the size of the core may be selected in view of a desired photoluminescent wavelength. For example, a size of the core may be greater than or equal to about 2 nm, greater than or equal to about 2.1 nm, greater than or equal to about 2.3 nm, greater than or equal to about 2.4 nm, greater than or equal to about 2.5 nm, greater than or equal to about 2.6 nm, greater than or equal to about 2.7 nm, greater than or equal to about 2.8 nm, greater than or equal to about 2.9 nm. For example, a size of the core may be less than or equal to about 4.5 nm, for example, less than or equal to about 4 nm, or less than or equal to about 3.5 nm. The core may include indium and phosphorous. The core may further include zinc.

The shell is a multi-layered shell. The shell may include a first semiconductor nanocrystal shell including zinc and selenium. The shell may include a second semiconductor nanocrystal shell disposed on or over the first semiconductor nanocrystal shell and including zinc and sulfur.

The first semiconductor nanocrystal shell may include (e.g., consist essentially, of, or consist of) ZnSe. The first semiconductor nanocrystal shell may not include sulfur (S), i.e., may be free of S or have no S added. In an embodiment, the first semiconductor nanocrystal shell may not include, i.e., may be free of ZnSeS. In other embodiments, the first semiconductor nanocrystal shell may include ZnSe, ZnSeS, or a combination thereof. The first semiconductor nanocrystal shell (e.g., consisting of ZnSe) may be disposed directly on the semiconductor nanocrystal core. The first semiconductor nanocrystal shell may have a thickness of greater than or equal to about 3 monolayer (ML), or greater than or equal to about 4 ML. A thickness of the first semiconductor nanocrystal shell may be less than or equal to about 10 ML, for example, less than or equal to about 9 ML, less than or equal to about 8 ML, less than or equal to about 7 ML, less than or equal to about 6 ML, less than or equal to about 5 ML, or less than or equal to about 4 ML.

The second semiconductor nanocrystal shell includes Zn and S. The second semiconductor nanocrystal shell may be disposed directly on the first semiconductor nanocrystal shell. The second semiconductor nanocrystal shell may have a composition varying in a radial direction. In an embodiment, the second semiconductor nanocrystal shell may include ZnS, ZnSeS, or a combination thereof. The second semiconductor nanocrystal shell may include at least two layers, and adjacent layers may have different composition from each other. In an embodiment, the second semiconductor nanocrystal shell may include the outermost layer consisting of ZnS.

In the cadmium free quantum dots of the embodiments, a molar ratio of zinc with respect to indium may be greater than or equal to about 10:1, for example, greater than or equal to about 11:1, greater than or equal to about 12:1, greater than or equal to about 13:1, greater than or equal to about 14:1, greater than or equal to about 15:1, greater than or equal to about 16:1, greater than or equal to about 17:1, greater than or equal to about 18:1, greater than or equal to about 19:1, greater than or equal to about 20:1, greater than or equal to about 21:1, greater than or equal to about 22:1, greater than or equal to about 23:1, greater than or equal to about 24:1, or greater than or equal to about 25:1. In the cadmium free quantum dots of the embodiments, a molar ratio of zinc with respect to indium may be less than or equal to about 60:1, for example, less than or equal to about 55:1, less than or equal to about 50:1, less than or equal to about 45:1, less than or equal to about 40:1, less than or equal to about 35:1, less than or equal to about 34:1, less than or equal to about 33:1, less than or equal to about 32:1, less than or equal to about 31:1, less than or equal to about 30:1, less than or equal to about 29:1, less than or equal to about 28:1, or less than or equal to about 27:1.

In the cadmium free quantum dots of the embodiments, a molar ratio of selenium with respect to indium may be greater than or equal to about 5.7:1, for example, greater than or equal to about 5.8:1, greater than or equal to about 5.9:1, greater than or equal to about 6.0:1, greater than or equal to about 6.1:1, greater than or equal to about 6.2:1, greater than or equal to about 6.3:1, greater than or equal to about 6.4:1, greater than or equal to about 6.5:1, greater than or equal to about 6.6:1, greater than or equal to about 6.7:1, greater than or equal to about 6.8:1, greater than or equal to about 6.9:1, greater than or equal to about 7.0:1, greater than or equal to about 8:1, greater than or equal to about 9:1, greater than or equal to about 10:1, greater than or equal to about 11:1, greater than or equal to about 12:1, or greater than or equal to about 13:1. In the cadmium free quantum dots of the embodiments, a molar ratio of selenium with respect to indium may be less than or equal to about 30:1, less than or equal to about 29:1, less than or equal to about 28:1, less than or equal to about 27:1, less than or equal to about 26:1, less than or equal to about 25:1, less than or equal to about 24:1, less than or equal to about 23:1, less than or equal to about 22:1, less than or equal to about 21:1, less than or equal to about 20:1, less than or equal to about 19:1, less than or equal to about 18:1, less than or equal to about 17:1, less than or equal to about 16:1, less than or equal to about 15:1, less than or equal to about 14:1, less than or equal to about 13:1, less than or equal to about 12:1, less than or equal to about 11:1, or less than or equal to about 10:1.

In the cadmium free quantum dots of the embodiments, a molar ratio of sulfur with respect to indium may be greater than or equal to about 2:1, for example, greater than or equal to about 3:1, greater than or equal to about 3.1:1, greater than or equal to about 3.2:1, greater than or equal to about 3.4:1, greater than or equal to about 4:1, or greater than or equal to about 5:1. In the cadmium free quantum dots of the embodiments, a molar ratio of sulfur with respect to indium may be less than or equal to about 20:1, for example, less than or equal to about 19:1, less than or equal to about 18:1, less than or equal to about 17:1, less than or equal to about 16:1, less than or equal to about 15:1, less than or equal to about 14:1, less than or equal to about 13:1, less than or equal to about 12:1, less than or equal to about 11:1, less than or equal to about 10:1, or less than or equal to about 9:1.

In the cadmium free quantum dots of the embodiments, a molar ratio of selenium with respect to sulfur may be greater than or equal to about 0.87:1, for example, greater than or equal to about 0.88:1, greater than or equal to about 0.89:1, greater than or equal to about 0.9:1, greater than or equal to about 1, greater than or equal to about 1.1:1, greater than or equal to about 1.2:1, greater than or equal to about 1.3:1, greater than or equal to about 1.4:1, greater than or equal to about 1.5:1, greater than or equal to about 1.6:1, or greater than or equal to about 1.7:1. In the cadmium free quantum dots of the embodiments, a molar ratio of selenium with respect to sulfur may be less than or equal to about 5:1, for example, less than or equal to about 4:1, less than or equal to about 3.5:1, less than or equal to about 3:1, less than or equal to about 2.5:1, or less than or equal to about 2:1.

In the cadmium free quantum dots of the embodiments, a molar ratio of the sum of selenium and sulfur with respect to indium [(S+Se)/In] may be greater than or equal to about 3:1, for example, greater than or equal to about 4:1, greater than or equal to about 5:1, greater than or equal to about 6, greater than or equal to about 7, greater than or equal to about 8, greater than or equal to about 9:1, greater than or equal to about 10:1, greater than or equal to about 11:1, greater than or equal to about 12:1, greater than or equal to about 13:1, greater than or equal to about 14:1, greater than or equal to about 15:1, greater than or equal to about 16:1, greater than or equal to about 17:1, greater than or equal to about 18:1, greater than or equal to about 19:1, greater than or equal to about 20:1, or greater than or equal to about 21:1. In the cadmium free quantum dots of the embodiments, a molar ratio of the sum of selenium and sulfur with respect to indium [(S+Se)/In] may be less than or equal to about 40:1, less than or equal to about 35:1, less than or equal to about 30:1, less than or equal to about 25:1, less than or equal to about 24:1, less than or equal to about 23:1, less than or equal to about 22:1, less than or equal to about 21:1, less than or equal to about 20:1, less than or equal to about 19:1, or less than or equal to about 18:1.

In the cadmium free quantum dots of the embodiments, a molar ratio of zinc with respect to the sum of selenium and sulfur [Zn/(S+Se)] may be greater than or equal to about 1:1 and less than or equal to about 1.5:1.

In an embodiment, the cadmium free quantum dot may not include boron, i.e., may be free of boron or have no boron added.

A display device based on the quantum dot may provide an improved display quality in terms of color purity, brightness, and the like. For example, a conventional liquid crystal display device (e.g., a conventional LCD device) is a device realizing color by polarized light that passes through a liquid crystal layer and a color filter, and has a problem of narrow viewing angle and lower brightness due to the low light transmittance of the absorptive color filter. The quantum dot has a theoretical quantum yield of about 100% and may emit light of high color purity (e.g., having a FWHM of less than or equal to about 40 nm), thereby realizing enhanced luminance efficiency and improved color purity. Thus, replacing the absorptive color filter with a photoluminescent type color filter including quantum dots may contribute a wider viewing angle and an increased brightness.

In order to be utilized in a device, however, the quantum dot may be processed into a form of a composite wherein a plurality of the quantum dots are dispersed in a host matrix (e.g., including a polymer and/or inorganic material). A quantum dot polymer composite or a color filter including the same may provide a display device having high brightness, wide viewing angle, and high color purity. The population of the cadmium free quantum dots may exhibit a relatively narrow FWHM and thus makes it possible to realize enhanced color purity even under a next generation color standard such as BT2020.

The cadmium free quantum dots may include an organic ligand. The organic ligand may bound to a surface of the quantum dot. The organic ligand may include a carboxylic acid compound and a primary amine compound. A carboxylic acid group of the carboxylic acid compound may include a C5 to C30 hydrocarbon group, and a primary amine group of the primary amine compound may include a C5 to C30 hydrocarbon group. The primary amine group may include a C5 to C30 alkenyl group.

The carboxylic acid compound may be represented by Chemical Formula 1 and the primary amine compound may be represented by Chemical Formula 2:

$$R^1COOH \qquad \text{Chemical Formula 1}$$

$$R^2NH_2 \qquad \text{Chemical Formula 2}$$

wherein $R^1$ and $R^2$ are the same or different and each independently a substituted or unsubstituted aliphatic hydrocarbon group (e.g., alkyl, alkenyl, or alkynyl) having a carbon number of greater than or equal to about 5 and less than or equal to about 40 or less than or equal to about 30, for example a substituted or unsubstituted C5 to C30 alkyl, alkenyl, or alkynyl group, a substituted or unsubstituted C5 to C30 alicyclic hydrocarbon group, a substituted or unsubstituted C6 to C30 aromatic hydrocarbon group (e.g., aryl), or a combination thereof.

The carboxylic acid compound may include pentanoic acid, hexanoic acid, heptanoic acid, octanoic acid, nonanoic acid, decanoic acid, undecanoic acid, dodecanoic acid, tridecanoic acid, tetradecanoic acid, pentadecanoic acid, hexadecanoic acid, heptadecanoic acid, octadecanoic acid, nonadecanoic acid, eicosanoic acid, heneicosanoic acid, docosanoic acid, tricosanoic acid, tetracosanoic acid, pentacosanoic acid, hexacosanoic acid, heptacosanoic acid, octacosanoic acid, nonacosanoic acid, triacontanoic acid, tetra-triacontanoic acid, pentatriacontanoic acid, hexatriacontanoic acid, alpha linolenic acid, eicosapentaenoic acid, docosahexaenoic acid, linolenic acid, gamma-linolenic acid, dihomo-gamma-linolenic acid, arachidonic acid, paullinic acid, oleic acid, elaidic acid, eicosenoic acid, erucic acid, nervonic acid, or a combination thereof.

The primary amine compound may include a pentylamine, hexylamine, heptylamine, octylamine, nonylamine, decylamine, undecylamine, dodecylamine, tridecylamine, pentadecylamine, hexadecylamine, heptadecylamine, ocatdecylamine, nonadecylamine, oleylamine, or a combination thereof.

The quantum dot may emit green light. The green light may have a maximum peak wavelength of greater than or equal to about 500 nm, for example, greater than or equal to about 510 nm, and less than or equal to about 600 nm, for example less than or equal to about 560 nm. The quantum dot may emit red light. The red light may have a maximum peak wavelength of greater than or equal to about 600 nm, for example, greater than or equal to about 610 nm, and less than or equal to about 650 nm, for example less than or equal to about 640 nm.

The cadmium free quantum dot may have a quantum yield of greater than or equal to about 80%, greater than or equal to about 81%, or greater than or equal to about 82%. The cadmium free quantum dot may have a FWHM of less than or equal to about 45 nm, for example, less than or equal to about 44 nm, less than or equal to about 43 nm, less than or equal to about 42 nm, or less than or equal to about 41 nm.

In the UV-Vis absorption spectrum of the cadmium free quantum dot, the first absorption peak may be present in a wavelength range of greater than or equal to about 450 nm and less than a photoluminescent peak wavelength of the cadmium free quantum dot. In an embodiment, a green light emitting quantum dot may have the first absorption peak wavelength that is for example, greater than or equal to about 480 nm, greater than or equal to about 485 nm, or greater than or equal to about 490 nm and less than or equal to about 520 nm, less than or equal to about 515 nm, or less than or equal to about 510 nm. In an embodiment, a red light emitting quantum dot may have the first absorption peak wavelength that is for example, greater than or equal to about 580 nm, greater than or equal to about 590 nm and less than or equal to about 620 nm, less than or equal to about 610 nm.

Another embodiment is directed to a method of producing the aforementioned population of the cadmium free quantum dots, which includes:

reacting a zinc containing precursor and a selenium containing precursor in the presence of a semiconductor nanocrystal core particle including indium and phosphorous in a heated organic solvent and an organic ligand at a first reaction temperature for a time period of greater than or equal to about 40 minutes to form a first semiconductor nanocrystal shell on the semiconductor nanocrystal core; and reacting a zinc containing precursor and a sulfur containing precursor in the presence of a particle having the first semiconductor nanocrystal shell formed on the core in the organic solvent and the organic ligand at a second reaction temperature to form a second semiconductor nanocrystal shell on the first semiconductor nanocrystal shell, wherein the organic ligand includes a carboxylic acid compound and a primary amine compound.

During the formation of the first semiconductor nanocrystal shell, the organic ligand may include the carboxylic acid compound and the primary amine compound.

In the aforementioned method, the amounts of the selenium containing precursor, the sulfur containing precursor, and the zinc containing precursor may be controlled so that the resulting quantum dots may have the molar ratios of the selenium and sulfur with respect to indium (or zinc) within the aforementioned ranges.

Details of the cadmium free quantum dots (e.g., their structure and the composition), the carboxylic acid compound, the primary amine compound, and the like are the same as set forth above.

In the reaction system, the amount of the carboxylic acid compound and the amount of the primary amine compound may be controlled with respect to the zinc containing precursor.

The carboxylic acid compound may be present in an amount greater than or equal to about 0.5 moles, greater than or equal to about 0.6 moles, greater than or equal to about 0.7 moles, greater than or equal to about 0.8 moles, greater than or equal to about 0.9 moles, greater than or equal to about 1 moles, greater than or equal to about 2 moles, greater than or equal to about 3 moles, and less than or equal to about 10 moles, for example, less than or equal to about 5 moles, and less than or equal to about 4 moles, per one mole of the zinc containing precursor. The primary amine compound may be present in an amount greater than or equal to about 0.5 moles, greater than or equal to about 0.6 moles, greater than or equal to about 0.7 moles, greater than or equal to about 0.8 moles, greater than or equal to about 0.9 moles, greater than or equal to about 1 moles, greater than or equal to about 2 moles, greater than or equal to about 3 moles, and less than or equal to about 10 moles, for example, less than or equal to about 5 moles, and less than or equal to about 4 moles, per one mole of the zinc containing precursor.

In an embodiment, the organic ligand may further include an additional organic ligand compound such as $R_2NH$, $R_3N$, RSH, $RH_2PO$, $R_2HPO$, $R_3PO$, $RH_2P$, $R_2HP$, $R_3P$, ROH, RCOOR', $RPO(OH)_2$, RHPOOH, $R_2POOH$, (wherein R and R' are the same or different, and are independently a hydrogen, C1 to C40 aliphatic hydrocarbon group, such as C1 to C40 (C3 to C24) alkyl or C2 to C40 (e.g., C3 to C24) alkenyl group, C2 to C40 (e.g., C3 to C24) alkynyl group or a C6 to C40 aromatic hydrocarbon group such as a C6 to C20 aryl group), a polymeric organic ligand, or a combination thereof.

Examples of the additional organic ligand compound may include:

a thiol compound such as methane thiol, ethane thiol, propane thiol, butane thiol, pentane thiol, hexane thiol, octane thiol, dodecane thiol, hexadecane thiol, octadecane thiol, benzyl thiol;

an amine compound such as dimethylamine, diethylamine, dipropylamine, tributylamine, trioctylamine, or a combination thereof;

a phosphine compound such as methyl phosphine, ethyl phosphine, propyl phosphine, butyl phosphine, pentyl phosphine, octyl phosphine, dioctyl phosphine, tributyl phosphine, trioctyl phosphine, or a combination thereof;

a phosphine oxide compound such as methyl phosphine oxide, ethyl phosphine oxide, propyl phosphine oxide, butyl phosphine oxide, pentyl phosphine oxide, tributyl phosphine oxide, octylphosphine oxide, dioctyl phosphine oxide, trioctyl phosphine oxide, or a combination thereof;

diphenyl phosphine, triphenyl phosphine, or an oxide compound thereof, or a combination thereof;

a mono- or di(C5 to C20 alkyl)phosphinic acid such as mono- or dihexylphosphinic acid, mono- or dioctylphosphinic acid, mono- or didodecylphosphinic acid, mono- or di(tetradecyl)phosphinic acid, mono- or di(hexadecyl)phosphinic acid, mono- or di(octadecyl)phosphinic acid, or a combination thereof;

a C5 to C20 alkylphosphonic acid such as hexylphosphonic acid, octylphosphonic acid, dodecylphosphonic acid, tetradecylphosphonic acid, hexadecylphosphonic acid, octadecylphosphonic acid, or a combination thereof;

or a combination thereof.

Examples of the organic solvent may include a C6 to C22 secondary amine such as dioctylamine, a C6 to C40 tertiary amine such as a trioctyl amine (TOA), a nitrogen-containing heterocyclic compound such as pyridine, a C6 to C40 olefin such as octadecene, a C6 to C40 aliphatic hydrocarbon such as hexadecane, octadecane, squalene, or squalane, an aromatic hydrocarbon substituted with a C6 to C30 alkyl group such as phenyldodecane, phenyltetradecane, or phenyl hexadecane, a primary, secondary, or tertiary phosphine (e.g., trioctyl phosphine) containing at least one (e.g., 1, 2, or 3) C6 to C22 alkyl group, a phosphine oxide (e.g., trioctylphosphine oxide) containing at least one (e.g., 1, 2, or 3) C6 to C22 alkyl group, a C12 to C22 aromatic ether such as a phenyl ether or a benzyl ether, or a combination thereof. The organic solvent may include a tertiary amine (e.g., trioctyl amine).

The organic solvent (e.g., including the zinc containing precursor and an organic ligand such as a carboxylic acid compound) may be heated to a predetermined temperature (e.g., of greater than or equal to about 100° C., for example, greater than or equal to about 120° C., greater than or equal to about 150° C., greater than or equal to about 200° C., greater than or equal to about 250° C., or greater than or equal to about 270° C.) and less than or equal to about the first reaction temperature under vacuum and/or an inert atmosphere. The heated organic solvent (e.g., including the zinc containing precursor and an organic ligand such as a carboxylic acid compound) may further include the primary amine compound.

Details of the semiconductor nanocrystal core including the indium and the phosphorous are the same as set forth above. The core may be commercially available or may be prepared in any appropriate method. The preparation of the core is not particularly limited and may be performed in any method of producing an indium phosphide based core. In some embodiment, the core may be synthesized in a hot injection manner wherein a solution including a metal precursor (e.g., an indium precursor) and optionally a ligand is heated at a high temperature (e.g., of greater than or equal to about 200° C.) and then a phosphorous precursor is injected the heated hot solution. In other embodiments, the synthesis of the core may adopt a low temperature injection method. The prepared core may be injected the heated organic solvent at a temperature of greater than or equal to about 100° C.

Types of the zinc containing precursor are not particularly limited and selected appropriately. In an embodiment, the zinc containing precursor may include a Zn metal powder, an alkylated Zn compound, Zn alkoxide, Zn carboxylate, Zn nitrate, Zn perchlorate, Zn sulfate, Zn acetylacetonate, Zn halide, Zn cyanide, Zn hydroxide, Zn oxide, Zn peroxide, Zn carbonate, or a combination thereof. Examples of the zinc containing precursor may include dimethyl zinc, diethyl zinc, zinc acetate, zinc acetylacetonate, zinc iodide, zinc bromide, zinc chloride, zinc fluoride, zinc carbonate, zinc cyanide, zinc nitrate, zinc oxide, zinc peroxide, zinc perchlorate, zinc sulfate, and the like. The zinc containing precursor may be used alone or in a combination of two or more compounds.

Types of the selenium containing precursor are not particularly limited and may be selected appropriately. For example, the selenium containing precursor may include selenium-trioctylphosphine (Se-TOP), selenium-tributylphosphine (Se-TBP), selenium-triphenylphosphine (Se-TPP), or a combination thereof, but is not limited thereto.

The first reaction temperature may be selected appropriately and, for example, may be greater than or equal to about 280° C., greater than or equal to about 290° C., greater than or equal to about 300° C., greater than or equal to about 310° C., or greater than or equal to about 315° C. and less than or equal to about 390° C., less than or equal to about 380° C., less than or equal to about 370° C., less than or equal to about 360° C., less than or equal to about 350° C., less than or equal to about 340° C., less than or equal to about 330° C.

After or during the heating to the first reaction temperature, a selenium containing precursor may be injected at least one time (e.g., at least twice, at least third times).

The reaction time at the first reaction temperature may be greater than or equal to about 40 minutes, for example, greater than or equal to about 50 minutes, greater than or equal to about 60 minutes, greater than or equal to about 70 minutes, greater than or equal to about 80 minutes, greater than or equal to about 90 minutes, and less than or equal to about 4 hours, for example, less than or equal to about 3 hours, less than or equal to about 2 hours.

By the reaction at the first reaction temperature for the aforementioned time period, the first semiconductor nanocrystal shell having a thickness of greater than or equal to about 3 ML may be formed.

In this case, the amount of the selenium containing precursor with respect to the indium may be controlled such that during the predetermined reaction time, the first semiconductor nanocrystal shell having the predetermined thickness may be formed. In an embodiment, the amount of the selenium per one mole of indium may be greater than or equal to about 7 moles, greater than or equal to about 8 moles, greater than or equal to about 9 moles, or greater than or equal to about 10 moles, but is not limited there to. In an embodiment, the amount of the selenium per one mole of indium may be less than or equal to about 40 moles, less than or equal to about 30 moles, less than or equal to about 25 moles, less than or equal to about 20 moles, less than or equal to about 18 moles, or less than or equal to about 15 moles, but is not limited thereto.

The method may not include lowering a temperature of a reaction mixture including the particle having the first semiconductor nanocrystal shell on the core to a temperature of below 100° C., for example, less than or equal to about 50° C., less than or equal to about 30° C., or at room temperature. In other words, the method may include maintaining a temperature of a reaction mixture including the particle having the first semiconductor nanocrystal shell on the core at a temperature of greater than or equal to 100° C., for example, greater than or equal to 50° C., greater than or equal to 30° C.

Types of the sulfur containing precursor are not particularly limited and may be selected appropriately. The sulfur containing precursor may include hexane thiol, octane thiol, decane thiol, dodecane thiol, hexadecane thiol, mercapto propyl silane, sulfur-trioctylphosphine (S-TOP), sulfur-tributylphosphine (S-TBP), sulfur-triphenylphosphine (S-TPP), sulfur-trioctylamine (S-TOA), trimethylsilyl sulfide, ammonium sulfide, sodium sulfide, or a combination thereof. The sulfur containing precursor may be injected at least on time (e.g., at least twice).

The second reaction temperature may be selected appropriately and, for example, may be greater than or equal to about 280° C., greater than or equal to about 290° C., greater than or equal to about 300° C., greater than or equal to about 310° C., or greater than or equal to about 315° C. and less than or equal to about 390° C., for example, less than or equal to about 380° C., less than or equal to about 370° C., less than or equal to about 360° C., less than or equal to about 350° C., less than or equal to about 340° C., or less than or equal to about 330° C. After or during the heating of the reaction mixture to the second reaction temperature, a sulfur containing precursor may be injected at least one time (e.g., at least twice, at least three times).

The reaction time at the second reaction temperature may be controlled appropriately. For example, the reaction time at the second reaction temperature may be greater than or equal to about 30 minutes, for example, greater than or equal to about 40 minutes, greater than or equal to about 50 minutes, greater than or equal to about 60 minutes, greater than or equal to about 70 minutes, greater than or equal to about 80 minutes, greater than or equal to about 90 minutes, and less than or equal to about 4 hours, for example, less than or equal to about 3 hours, less than or equal to about 2 hours.

In an embodiment, the amount of sulfur with respect to one mole of indium may be greater than or equal to about 5 moles, greater than or equal to about 6 moles, greater than or equal to about 7 moles, greater than or equal to about 8 moles, greater than or equal to about 9 moles, greater than or equal to about 10 moles, greater than or equal to about 11 moles, greater than or equal to about 12 moles, greater than or equal to about 13 moles, greater than or equal to about 14 moles, greater than or equal to about 15 moles, greater than or equal to about 16 moles, greater than or equal to about 17 moles, greater than or equal to about 18 moles, greater than or equal to about 19 moles, or greater than or equal to about 20 moles, but is not limited there to. In an embodiment, the amount of sulfur with respect to one mole of indium in a reaction mixture including the particle having the first semiconductor nanocrystal shell on the core may be less than or equal to about 45 moles, less than or equal to about 40 moles, or less than or equal to about 35 moles, but is not limited there to.

An amount of the zinc containing precursor with respect to the indium may be controlled and selected considering the amounts of the selenium containing precursor and the sulfur containing precursor, the properties and the structure of the final quantum dot.

When the non-solvent is added into the obtained final reaction solution, the organic ligand-coordinated nanocrystal may be separated (e.g., precipitated). The non-solvent may be a polar solvent that is miscible with the solvent used in the reaction and nanocrystals are not dispersible therein. The non-solvent may be selected depending on the solvent used in the reaction and may be for example, acetone, ethanol, butanol, isopropanol, ethanediol, water, tetrahydrofuran (THF), dimethylsulfoxide (DMSO), diethylether, formaldehyde, acetaldehyde, a solvent having a similar solubility parameter to the foregoing solvents, or a combination thereof. The separation may be performed through a centrifugation, precipitation, chromatography, or distillation. The separated nanocrystal may be added to a washing solvent and washed, if desired. The washing solvent is not particularly limited and may include a solvent having a similar solubility parameter to that of the ligand and may, for example, include hexane, heptane, octane, chloroform, toluene, benzene, and the like.

The population of the quantum dots may be dispersed in a dispersing solvent. The population of the quantum dots may form an organic solvent dispersion. The organic solvent dispersion may be free of water and/or may be free of a water miscible organic solvent. The dispersing solvent may be selected appropriately. The dispersing solvent may include (or consists of) the aforementioned organic solvent. The dispersing solvent may include (or consists of) a substituted or unsubstituted C1 to C40 aliphatic hydrocarbon, a substituted or unsubstituted C6 to C40 aromatic hydrocarbon, or a combination thereof.

In another embodiment, a quantum dot composition includes: the aforementioned population of the cadmium free quantum dots; a polymerizable (e.g., photopolymerizable) monomer including a carbon-carbon double bond; and optionally a binder polymer; and optionally an initiator (e.g., a photoinitiator). The composition may further include an organic solvent and/or a liquid vehicle. The composition may be photosensitive.

In the composition, details for the population of the cadmium free quantum dots are the same as set forth above. In the composition, the amount of the quantum dot may be selected appropriately in light of the types and amounts of other components in the composition and a final use thereof. In an embodiment, the amount of the quantum dot may be greater than or equal to about 1 wt %, for example, greater than or equal to about 2 wt %, greater than or equal to about 3 wt %, greater than or equal to about 4 wt %, greater than or equal to about 5 wt %, greater than or equal to about 6 wt %, greater than or equal to about 7 wt %, greater than or equal to about 8 wt %, greater than or equal to about 9 wt %, greater than or equal to about 10 wt %, greater than or equal to about 15 wt %, greater than or equal to about 20 wt %, greater than or equal to about 25 wt %, greater than or equal to about 30 wt %, greater than or equal to about 35 wt %, or greater than or equal to about 40 wt %, based on a total solid content of the composition. The amount of the quantum dot may be less than or equal to about 70 wt %, for example, less than or equal to about 65 wt %, less than or equal to about 60 wt %, less than or equal to about 55 wt %, or less than or equal to about 50 wt %, based on a total solid content of the composition.

In the composition of the embodiments, the binder polymer may include a carboxylic acid group (e.g., a carboxylic acid group containing polymer). In an embodiment, the binder polymer may include:

a copolymer of a monomer combination including a first monomer, a second monomer, and optionally a third monomer, the first monomer having a carboxylic acid group and a carbon-carbon double bond, the second monomer having a carbon-carbon double bond and a hydrophobic moiety and not having a carboxylic acid group, and the third monomer having a carbon-carbon double bond and a hydrophilic moiety and not having a carboxylic acid group;

a multi-aromatic ring-containing polymer including a carboxylic acid group (—COOH) and having a backbone structure in a main chain (e.g., a backbone structure incorporated in the main chain), wherein the backbone structure includes a cyclic group including a quaternary carbon atom and two aromatic rings bound to the quaternary carbon atom;

or a combination thereof.

Examples of the first monomer may include, but are not limited to, acrylic acid, methacrylic acid, maleic acid, itaconic acid, fumaric acid, 3-butenoic acid, and other carboxylic acid vinyl ester compounds. The first monomer may include one or more compounds.

Examples of the second monomer may include, but are not limited to:

alkenyl aromatic compounds such as styrene, α-methyl styrene, vinyl toluene, or vinyl benzyl methyl ether;

unsaturated carboxylic acid ester compounds such as methyl acrylate, methyl methacrylate, ethyl acrylate, ethyl methacrylate, butyl acrylate, butyl methacrylate, benzyl acrylate, benzyl methacrylate, cyclohexyl acrylate, cyclohexyl methacrylate, phenyl acrylate, or phenyl methacrylate;

unsaturated carboxylic acid amino alkyl ester compounds such as 2-amino ethyl acrylate, 2-amino ethyl methacrylate, 2-dimethyl amino ethyl acrylate, or 2-dimethyl amino ethyl methacrylate;

maleimides such as N-phenylmaleimide, N-benzylmaleimide, N-alkylmaleimide;

unsaturated carboxylic acid glycidyl ester compounds such as glycidyl acrylate or glycidyl methacrylate;

vinyl cyanide compounds such as acrylonitrile or methacrylonitrile; and unsaturated amide compounds such as acrylamide or methacrylamide, but are not limited thereto.

As the second monomer, at least one compound may be used.

If present, examples of the third monomer may include 2-hydroxy ethyl acrylate, 2-hydroxy ethyl methacrylate, hydroxy propyl acrylate, hydroxy propyl methacrylate, hydroxy butyl acrylate, and hydroxy butyl methacrylate, but are not limited thereto. The third monomer may include one or more compounds.

In an embodiment, in the binder polymer, an amount of the first repeating unit derived from the first monomer may be greater than or equal to about 5 mole percent (mol %), for example, greater than or equal to about 10 mol %, greater than or equal to about 15 mol %, greater than or equal to about 25 mol %, or greater than or equal to about 35 mol %. In the binder polymer, an amount of the first repeating unit may be less than or equal to about 95 mol %, for example, less than or equal to about 90 mol %, less than or equal to about 89 mol %, less than or equal to about 88 mol %, less than or equal to about 87 mol %, less than or equal to about 86 mol %, less than or equal to about 85 mol %, less than or equal to about 80 mol %, less than or equal to about 70 mol %, less than or equal to about 60 mol %, less than or equal to about 50 mol %, less than or equal to about 40 mol %, less than or equal to about 35 mol %, or less than or equal to about 25 mol %.

In the binder polymer, an amount of the second repeating unit derived from the second monomer may be greater than or equal to about 5 mol %, for example, greater than or equal to about 10 mol %, greater than or equal to about 15 mol %, greater than or equal to about 25 mol %, or greater than or equal to about 35 mol %. In the binder polymer, an amount of the second repeating unit may be less than or equal to about 95 mol %, for example, less than or equal to about 90 mol %, less than or equal to about 89 mol %, less than or equal to about 88 mol %, less than or equal to about 87 mol %, less than or equal to about 86 mol %, less than or equal to about 85 mol %, less than or equal to about 80 mol %, less than or equal to about 70 mol %, less than or equal to about 60 mol %, less than or equal to about 50 mol %, less than or equal to about 40 mol %, less than or equal to about 35 mol %, or less than or equal to about 25 mol %.

In the binder polymer, an amount of the third repeating unit derived from the third monomer, when present, may be greater than or equal to about 1 mol %, for example, greater than or equal to about 5 mol %, greater than or equal to about 10 mol %, or greater than or equal to about 15 mol %. In the binder polymer, an amount of the third repeating unit, when present, may be less than or equal to about 30 mol %, for example, less than or equal to about 25 mol %, less than or equal to about 20 mol %, less than or equal to about 18 mol %, less than or equal to about 15 mol %, or less than or equal to about 10 mol %.

In an embodiment, the carboxylic acid group-containing binder may include a copolymer of (meth)acrylic acid and at least one second or third monomer including an (C6-C9 aryl) or (C1-C10 alkyl)(meth)acrylate, hydroxyl(C1-C10 alkyl) (meth)acrylate, or styrene. For example, the binder polymer may include a (meth)acrylic acid/methyl (meth) acrylate copolymer, a (meth)acrylic acid/benzyl (meth)acrylate copolymer, a (meth)acrylic acid/benzyl (meth)acrylate/ styrene copolymer, a (meth)acrylic acid/benzyl (meth) acrylate/2-hydroxy ethyl (meth)acrylate copolymer, a (meth)acrylic acid/benzyl (meth)acrylate/styrene/2-hydroxy ethyl (meth)acrylate copolymer, or a combination thereof.

In an embodiment, the carboxylic acid group containing binder may include a multi-aromatic ring-containing polymer. The multi-aromatic ring-containing polymer may include a carboxylic acid group (—COOH) and a main chain having a backbone structure incorporated therein, wherein the backbone structure includes a cyclic group including a quaternary carbon atom, which is a part of the cyclic group, and two aromatic rings bound to the quaternary carbon atom. The carboxylic acid group may be bonded to the main chain. The multi-aromatic ring-containing polymer is also known as a cardo binder, which may be synthesized by a known method or is commercially available (e.g., from Nippon Steel Chemical Co., Ltd.).

The carboxylic acid group-containing binder may have an acid value of greater than or equal to about 50 mg KOH/g. For example, the carboxylic acid group-containing binder may have an acid value of greater than or equal to about 60 mg KOH/g, greater than or equal to about 70 mg KOH/g, greater than or equal to about 80 mg KOH/g, greater than or equal to about 90 mg KOH/g, greater than or equal to about 100 mg KOH/g, greater than or equal to about 110 mg KOH/g, greater than or equal to about 120 mg KOH/g, greater than or equal to about 125 mg KOH/g, or greater than or equal to about 130 mg KOH/g, but is not limited thereto. The carboxylic acid group-containing binder may have an acid value of less than or equal to about 250 mg KOH/g, for example, less than or equal to about 240 mg KOH/g, less than or equal to about 230 mg KOH/g, less than or equal to about 220 mg KOH/g, less than or equal to about 210 mg KOH/g, less than or equal to about 200 mg KOH/g, less than or equal to about 190 mg KOH/g, less than or equal to about 180 mg KOH/g, or less than or equal to about 160 mg KOH/g, but is not limited thereto.

The binder polymer (e.g., containing the carboxylic acid group, such as the carboxylic acid group-containing binder) may have a molecular weight of greater than or equal to about 1,000 grams per mole (g/mol), for example, greater than or equal to about 2,000 g/mol, greater than or equal to about 3,000 g/mol, or greater than or equal to about 5,000 g/mol. The binder polymer may have a molecular weight of less than or equal to about 100,000 g/mol, for example, less than or equal to about 50,000 g/mol.

In the composition, if present, an amount of the carboxylic acid group-containing binder may be greater than or equal to about 0.5 wt %, for example, greater than or equal to about 1 wt %, greater than or equal to about 5 wt %, greater than or equal to about 10 wt %, greater than or equal to about 15 wt %, or greater than or equal to about 20 wt %, based on the total weight of the composition. In an embodiment, an amount of the carboxylic acid group-containing binder may less than or equal to about 50 wt %, less than or equal to about 40 wt %, less than or equal to about 35 wt %, less than or equal to about 33 wt %, or less than or equal to about 30 wt %, based on the total weight of the composition. The amount of the binder polymer may be greater than or equal to about 0.5 wt % and less than or equal to about 55%, based on a total solid content of the composition.

In the composition according to an embodiment, the (photo)polymerizable monomer having at least one (e.g., at least two, at least three, or more) carbon-carbon double bond may include a (meth)acrylate monomer. Examples of the photopolymerizable monomer may include, but are not limited to, C1-C10-alkyl (meth)acrylate, ethylene glycol di(meth)acrylate, triethylene glycol di(meth)acrylate, diethylene glycol di(meth)acrylate, 1,4-butanediol di(meth)acrylate, 1,6-hexanediol di(meth)acrylate, neopentyl glycol di(meth)acrylate, pentaerythritol di(meth)acrylate, pentaerythritol tri(meth)acrylate, pentaerythritol tetra(meth) acrylate, dipentaerythritol di(meth)acrylate, dipentaerythritol tri(meth)acrylate, dipentaerythritol penta(meth)acrylate, dipentaerythritol hexa(meth)acrylate, bisphenol A epoxy (meth)acrylate, bisphenol A di(meth)acrylate, trimethylolpropane tri(meth)acrylate, ethylene glycol monomethyl ether (meth)acrylate, novolac epoxy (meth)acrylate, propylene glycol di(meth)acrylate, tris(meth)acryloyloxyethyl phosphate, or a combination thereof.

The amount of the (photo)polymerizable monomer may be greater than or equal to about 0.5 wt %, for example, greater than or equal to about 1 wt %, or greater than or equal to about 2 wt % with respect to a total weight of the composition. The amount of the photopolymerizable monomer may be less than or equal to about 50 wt %, for example, less than or equal to about 40 wt %, less than or equal to about 30 wt %, less than or equal to about 28 wt %, less than or equal to about 25 wt %, less than or equal to about 23 wt %, less than or equal to about 20 wt %, less than or equal to about 18 wt %, less than or equal to about 17 wt %, less than or equal to about 16 wt %, or less than or equal to about 15 wt % with respect to a total weight of the composition.

The (photo) initiator included in the composition may be a compound that can initiate a radical polymerization of the (photo)polymerizable monomer and/or a thiol compound (e.g., by light). Types of the initiator are not particularly limited and may be selected appropriately. For example, the initiator may be a photo-initiator and may include a triazine compound, an acetophenone compound, a benzophenone compound, a thioxanthone compound, a benzoin compound, an oxime compound, an aminoketone compound, a phosphine or phosphine oxide compound, a carbazole compound, a diketone compound, a sulfonium borate compound, a diazo compound, a diimidazole compound, or a combination thereof, but it is not limited thereto. As an alternative to, or in addition to the foregoing photoinitiators, a carbazole compound, a diketone compound, a sulfonium borate compound, an azo compound (e.g., diazo compound), a biimidazole compound, or a combination thereof may be used as a photoinitiator.

In the composition of the embodiments, an amount of the initiator may be adjusted in light of the types and the amount of the photopolymerizable monomer as used. In an embodiment, the amount of the initiator may be greater than or equal to about 0.01 wt % or greater than or equal to about 1 wt % and less than or equal to about 10 wt %, less than or equal to about 9 wt %, less than or equal to about 8 wt %, less than or equal to about 7 wt %, less than or equal to about 6 wt %, or less than or equal to about 5 wt % based on a total weight of the composition, but is not limited thereto.

The (photosensitive) composition may further include a thiol compound having at least one thiol group (e.g., monothiol or multi-thiol compound), a metal oxide fine particle, or a combination thereof.

When a plurality of metal oxide fine particles is present in the polymer matrix, the metal oxide fine particles may include $TiO_2$, $SiO_2$, $BaTiO_3$, $Ba_2TiO_4$, ZnO, or a combination thereof. An amount of the metal oxide fine particle may be less than or equal to about 25 wt %, less than or equal to about 20 wt %, less than or equal to about 15 wt % and greater than or equal to about 1 wt %, or greater than or equal to about 5 wt % based on a total solid content of the composition. A particle size of the metal oxide fine particles is not particularly limited and may be selected appropriately. The particle size of the metal oxide fine particles may greater than or equal to about 100 nm, greater than or equal to about 150 nm, or greater than or equal to about 200 nm and less than or equal to about 1,000 nm, less than or equal to about 900 nm, or less than or equal to about 800 nm.

The multi-thiol compound may include a dithiol compound, a trithiol compound, a tetrathiol compound, or a combination thereof. For example, the multi-thiol compound may include glycol di-3-mercaptopropionate (e.g., ethylene glycol di-3-mercaptopropionate), glycol dimercaptoacetate (e.g., ethylene glycol dimercaptoacetate), trimethylolpropane tris(3-mercaptopropionate), pentaerythritol tetrakis(3-mercaptopropionate), pentaerythritol tetrakis(2-mercaptoacetate), 1,6-hexanedithiol, 1,3-propanedithiol, 1,2-ethanedithiol, polyethylene glycol dithiol including 1 to 10 ethylene glycol repeating units, or a combination thereof.

Based on a total weight of the composition, an amount of the thiol compound may be less than or equal to about 50 wt %, less than or equal to about 40 wt %, less than or equal to about 30 wt %, less than or equal to about 20 wt %, less than or equal to about 10 wt %, less than or equal to about 9 wt %, less than or equal to about 8 wt %, less than or equal to about 7 wt %, less than or equal to about 6 wt %, or less than or equal to about 5 wt %. The amount of the thiol compound may be greater than or equal to about 0.1 wt %, for example, greater than or equal to about 0.5 wt %, greater than or equal to about 1 wt %, greater than or equal to about 2 wt %, greater than or equal to about 3 wt %, greater than or equal to about 4 wt %, greater than or equal to about 5 wt %, greater than or equal to about 6 wt %, greater than or equal to about 7 wt %, greater than or equal to about 8 wt %, greater than or equal to about 9 wt %, or greater than or equal to about 10 wt %, based on a total weight of the composition.

The composition may further include an organic solvent and/or a liquid vehicle (hereinafter, simply referred to as "organic solvent"). Types of the organic solvent and/or the liquid vehicle are not particularly limited. Types and amounts of the organic solvent may be appropriately selected by considering the aforementioned main components (i.e., the quantum dot, the COOH group-containing binder, the photopolymerizable monomer, the photoinitiator, and if used, the thiol compound), and types and amounts of additives which will be described below. The composition may include a solvent in a residual amount except for a desired amount of the solid content (non-volatile components). The solvent may be appropriately selected by considering the other components (e.g., a binder, a photopolymerizable monomer, a photoinitiator, and other additives) in the composition, affinity for an alkali-developing solution, a boiling point, and the like. Non-limiting examples of the solvent and the liquid vehicle may include, but are not limited to: ethyl 3-ethoxy propionate; an ethylene glycol series such as ethylene glycol, diethylene glycol, or polyethylene glycol; a glycol ether such as ethylene glycol monomethyl ether, ethylene glycol monoethyl ether, diethylene glycol monomethyl ether, ethylene glycol diethyl ether, and diethylene glycol dimethyl ether; glycol ether acetates such as ethylene glycol monomethyl ether acetate, ethylene glycol monoethyl ether acetate, diethylene glycol monoethyl ether acetate, and diethylene glycol monobutyl ether acetate; a propylene glycol series such as propylene glycol; a propylene glycol ether such as propylene glycol monomethyl ether, propylene glycol monoethyl ether, propylene glycol monopropyl ether, propylene glycol monobutyl ether, propylene glycol dimethyl ether, dipropylene glycol dimethyl ether, propylene glycol diethyl ether, and dipropylene glycol diethyl ether; a propylene glycol ether acetate such as propylene glycol monomethyl ether acetate and dipropylene glycol monoethyl ether acetate; an amide such as N-methylpyrrolidone, dimethyl formamide, and dimethyl acetamide; a ketone such as methyl ethyl ketone (MEK), methyl isobutyl ketone (MIBK), and cyclohexanone; a petroleum product such as toluene, xylene, and solvent naphtha; an ester such as ethyl acetate, propyl acetate, butyl acetate, cyclohexyl acetate, and ethyl lactate; an ether such as diethyl ether, dipropyl ether, and dibutyl ether; chloroform, a C1 to C40 aliphatic hydrocarbon (e.g., alkane, alkene, or alkyne), a halogen (e.g., chloro) substituted C1 to C40 aliphatic hydrocarbon (e.g., dichloroethane, trichloromethane, and the like), a C6 to C40 aromatic hydrocarbon (e.g., toluene, xylene, and the like), a halogen (e.g., chloro) substituted C6 to C40 aromatic hydrocarbon, or a combination thereof.

The composition may further include various additives such as a light diffusing agent, a leveling agent, or a coupling agent, in addition to the aforementioned components. The amount of the additive is not particularly limited, and may be selected within an appropriate range, wherein the additive does not cause an adverse effect on the preparation of the composition, the preparation of the quantum dot polymer composite, and optionally, the patterning of the composite. Types and examples of the aforementioned additives may include any compound having a desired function and are not particularly limited.

If present, the amount of the additives may be, based on a total weight of the composition (or a solid content of the composition), greater than or equal to about 0.1 wt %, for example, greater than or equal to about 0.5 wt %, greater than or equal to about 1 wt %, greater than or equal to about 2 wt %, or greater than or equal to about 5 wt %, but it is not limited thereto. If present, the amount of the additives may be less than or equal to about 20 wt %, for example, less than or equal to about 19 wt %, less than or equal to about 18 wt %, less than or equal to about 17 wt %, less than or equal to about 16 wt %, or less than or equal to about 15 wt %, but it is not limited thereto.

The composition may be prepared by mixing the aforementioned components appropriately. The composition according to the embodiments may provide a quantum dot polymer composite or a quantum dot pattern via polymerization (e.g., photopolymerization).

In an embodiment, a quantum dot polymer composite may include a polymer matrix; and the aforementioned population of cadmium free quantum dots dispersed in the polymer matrix.

The polymer matrix may include a binder polymer; a polymerization product of a photopolymerizable monomer including at least one (e.g., at least two, three, four, or five or more) carbon-carbon double bond (s); optionally a polymerization product of the photopolymerizable monomer and a multi-thiol compound having at least two thiol groups at its terminal ends; or a combination thereof. In an embodiment, the polymer matrix may include a crosslinked polymer and optionally (a carboxylic acid group containing) binder polymer. The crosslinked polymer may include a thiolene polymer, a (meth)acrylate polymer, or a combination thereof. In an embodiment, the crosslinked polymer may include a polymerization product of the aforementioned photopolymerizable monomer and optionally the multi-thiol compound. Details of the binder polymer are the same as set forth above.

Details of the cadmium free quantum dot, the binder polymer, the photopolymerizable monomer, the multi-thiol compound are the same as set forth above.

A blue light absorption rate of the quantum dot polymer composite with respect to light having a wavelength of 450 nm may be greater than or equal to about 82%, for example, greater than or equal to about 83%, greater than or equal to about 84%, greater than or equal to about 85%, greater than or equal to about 86%, greater than or equal to about 87%, greater than or equal to about 88%, or greater than or equal to about 89%, for example when an amount of the cadmium free quantum dot is about 45% or less based on a total weight of the composite).

The quantum dot polymer composite may be in a form of a film or a sheet.

The film of the quantum dot polymer composite or a pattern thereof may have, for example, a thickness of less than or equal to about 30 μm, for example, less than or equal to about 10 μm, less than or equal to about 8 μm, or less than or equal to about 7 μm and greater than about 2 μm, for example, greater than or equal to about 3 μm, greater than or equal to about 3.5 μm, or greater than or equal to about 4 μm.

The sheet may have a thickness of less than or equal to about 1000 μm, for example, less than or equal to about 900 μm, less than or equal to about 800 μm, less than or equal to about 700 μm, less than or equal to about 600 μm, less than or equal to about 500 μm, or less than or equal to about 400 μm. The sheet may have a thickness of greater than or equal to about 10 μm, greater than or equal to about 50 μm, or greater than or equal to about 100 μm.

The quantum dot polymer composite may exhibit improved thermal stability. Accordingly, the quantum dot polymer composite may exhibit photo-conversion efficiency (PCE) of greater than or equal to about 20%, for example, greater than or equal to about 25%, greater than or equal to about 30%, when being heat-treated at about 180° C. for about 30 minutes under a nitrogen atmosphere.

In another embodiment, a display device includes a light source and a light emitting element (e.g., a photoluminescent element), and the light emitting element includes the above quantum dot-polymer composite, and the light source is configured to provide the light emitting element with incident light. The incident light may have a photoluminescence peak wavelength of greater than or equal to about 440 nm, for example, greater than or equal to about 450 nm and less than or equal to about 460 nm.

Figure 3:
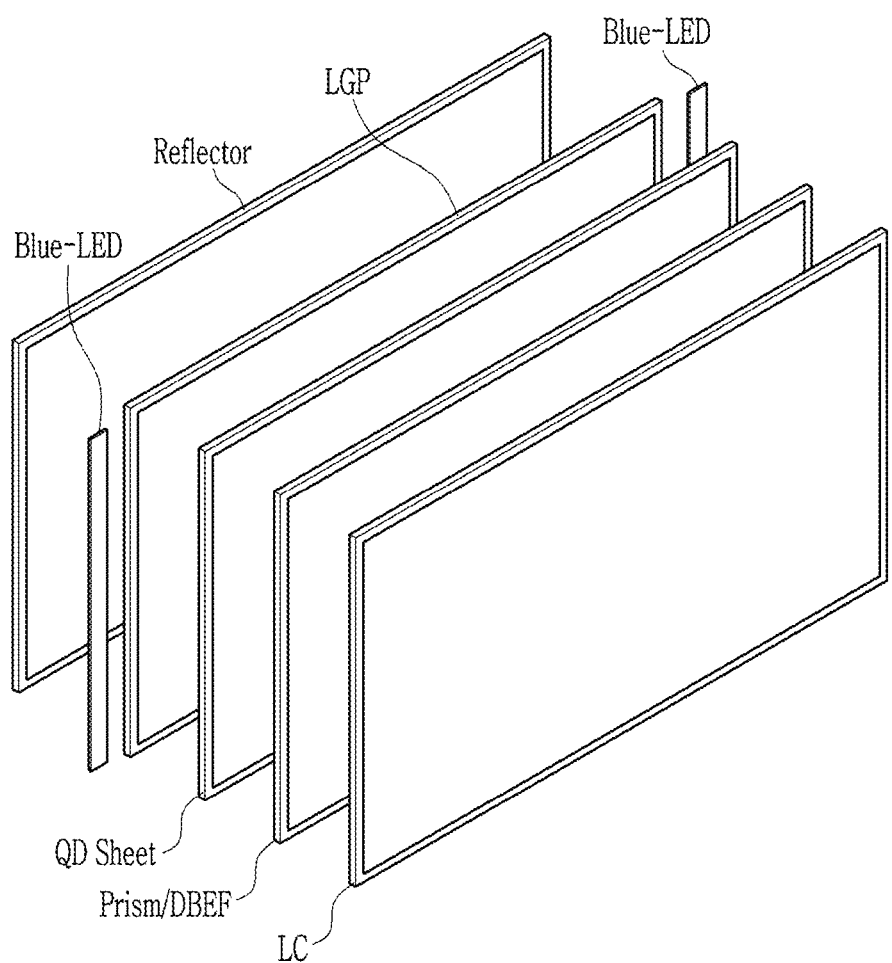
FIG. 3 is an exploded view of a display device according to an embodiment.

In an embodiment, the light emitting element may include a sheet of the quantum dot polymer composite. The display device may further include a liquid crystal panel and the sheet of the quantum dot polymer composite may be disposed between the light source and the liquid crystal panel. FIG. 3 shows an exploded view of a non-limiting display device. Referring to FIG. 3, the display device may have a structure wherein a reflector, a light guide panel (LGP) and a blue LED light source (Blue-LED), the quantum dot-polymer composite sheet (QD sheet), for example, various optical films such as a prism, double brightness enhance film (DBEF), and the like are stacked and a liquid crystal panel is disposed thereon.

In another embodiment, the display device may include a stacked structure including a (e.g., transparent) substrate and a light emitting layer (e.g., a photoluminescent layer) disposed on the substrate as a light emitting element. In the stacked structure, the light emitting layer includes a pattern of the quantum dot polymer composite, and the pattern may include at least one repeating section configured to emit light of a predetermined wavelength. The pattern of the quantum dot polymer composite may include at least one repeating section selected from a first section that may emit a first light and a second section that may emit a second light.

The first light and the second light have a different maximum photoluminescence peak wavelength in a photoluminescence spectrum. In an embodiment, the first light (R) may be red light present at a maximum photoluminescence peak wavelength of about 600 nm to about 650 nm (e.g., about 620 nm to about 650 nm), the second light (G) may be green light present at a maximum photoluminescence peak wavelength of about 500 nm to about 550 nm (e.g., about 510 nm to about 550 nm), or vice versa (i.e., the first light may be a green light and the second light may be a red light).

The substrate may be a substrate including an insulation material. The substrate may include a material such as glass; various polymers such as a polyester (e.g., poly(ethylene terephthalate) (PET), poly(ethylene naphthalate) (PEN), or the like), polycarbonate, a poly(C1 to C10 alkyl (meth)acrylate), polyimide, polyamide, or a combination thereof (a copolymer or a mixture thereof); polysiloxane (e.g., PDMS); an inorganic material such as $Al_2O_3$ or ZnO; or a combination thereof, but is not limited thereto. A thickness of the substrate may be desirably selected considering a substrate material but is not particularly limited. The substrate may have flexibility. The substrate may have a transmittance of greater than or equal to about 50%, greater than or equal to about 60%, greater than or equal to about 70%, greater than or equal to about 80%, or greater than or equal to about 90% for light emitted from the quantum dot.

At least a portion of the substrate may be configured to cut (absorb or reflect) blue light. A layer capable of blocking (e.g., absorbing or reflecting) blue light, also referred to herein as a "blue cut layer" or "blue light absorption layer", may be disposed on at least one surface of the substrate. For example, the blue cut layer (blue light absorption layer) may include an organic material and a predetermined dye, such as, for example, a yellow dye or a dye capable of absorbing blue light and transmitting green and/or red light.

In another embodiment, a method of producing the stacked structure includes forming a film of the above composition on a substrate;

exposing a selected region of the film to light (e.g., having a wavelength of less than or equal to about 400 nm); and developing the exposed film with an alkali developing solution to obtain a pattern of the quantum dot polymer composite.

The substrate and the composition have the same specification as described above.

Figure 4:
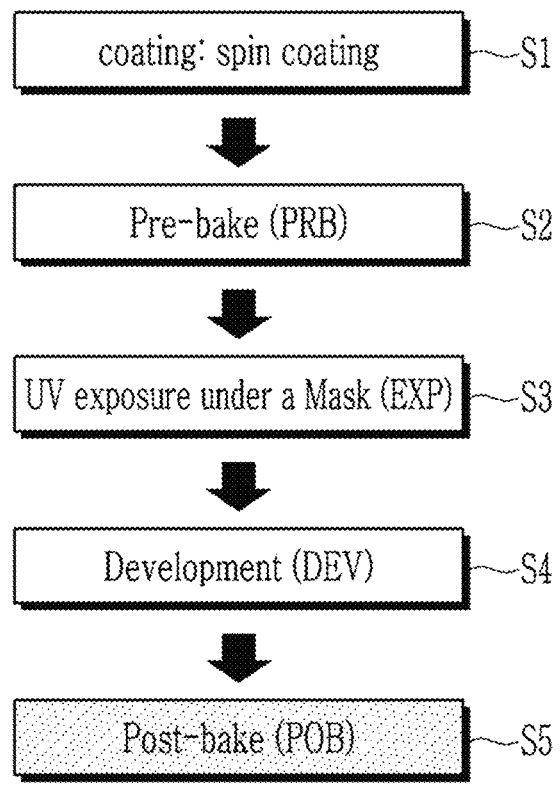
FIG. 4 is a view illustrating a process of producing a quantum dot polymer composite pattern using a composition according to an embodiment.
Figure 4:

A non-limiting method of forming a pattern of the quantum dot polymer composite is explained with reference to FIG. 4.

The composition is coated to have a predetermined thickness on a substrate in an appropriate method of spin coating, slit coating, and the like (S1). If desired, the formed film may be pre-baked (S2). Conditions (such as a temperature, a duration, and an atmosphere) for the pre-baking may be selected appropriately.

The formed (and optionally, pre-baked) film is exposed to light of a predetermined wavelength (UV light) under a mask having a predetermined pattern (S3). The wavelength and the intensity of light may be selected depending on the types and the amounts of the photoinitiator, the types and the amounts of quantum dots, or the like.

The film having the exposed selected area is treated (e.g., sprayed or immersed) with an alkali developing solution (S4), and thereby the unexposed region in the film is dissolved to provide a desired pattern. The obtained pattern may be post-baked (S5), if desired, to improve crack resistance and solvent resistance of the pattern, for example, at a temperature of about 150° C. to about 230° C. for a predetermined time, for example, greater than or equal to about 10 min or greater than or equal to about 20 min.

When the quantum dot-polymer composite pattern has a plurality of repeating sections, a quantum dot-polymer composite having a desired pattern may be obtained by preparing a plurality of compositions including a quantum dot (e.g., a red light emitting quantum dot, a green quantum dot, or optionally, a blue quantum dot) having desired photoluminescence properties (a photoluminescence peak wavelength and the like) to form each repeating section and repeating the pattern formation process for each of the composition as many times (e.g., twice or more or three times or more) as required to form a desired pattern of the quantum dot polymer composite (S6).

In another embodiment, an ink composition of an embodiment including the population of the cadmium free quantum dots and the liquid vehicle may be used to form a pattern. For example, a pattern may be formed by depositing the ink including nanomaterials (e.g., plurality of cadmium free quantum dots) and a liquid vehicle and a monomer on a desired region of a substrate and optionally removing the liquid vehicle and/or conducting a polymerization.

For example, the quantum dot-polymer composite may be in the form of a pattern of at least two different repeating color sections (e.g., RGB sections). Such a quantum dot-polymer composite pattern may be used as a photoluminescence-type color filter in a display device.

In other embodiments, a display device includes a light source and a light emitting element including a stacked structure.

The light source may be configured to provide incident light to the light emitting element including the stacked structure. The incident light may have a wavelength of about 440 nm to about 480 nm such as about 440 nm to about 470 nm. The incident light may be the third light.

In a display device including the stacked structure, the light source may include a plurality of light emitting units respectively corresponding to the first section and the second section, and the light emitting units may include a first electrode and a second electrode facing each other and an electroluminescent layer disposed between the first electrode and the second electrode. The electroluminescent layer may include an organic light emitting material.

For example, each light emitting unit of the light source may include an electroluminescent device (e.g., an organic light emitting diode (OLED)) structured to emit light of a predetermined wavelength (e.g., blue light, green light, or a combination thereof). Structures and materials of the electroluminescent device and the organic light emitting diode (OLED) are known but not particularly limited.

Figure 5A:
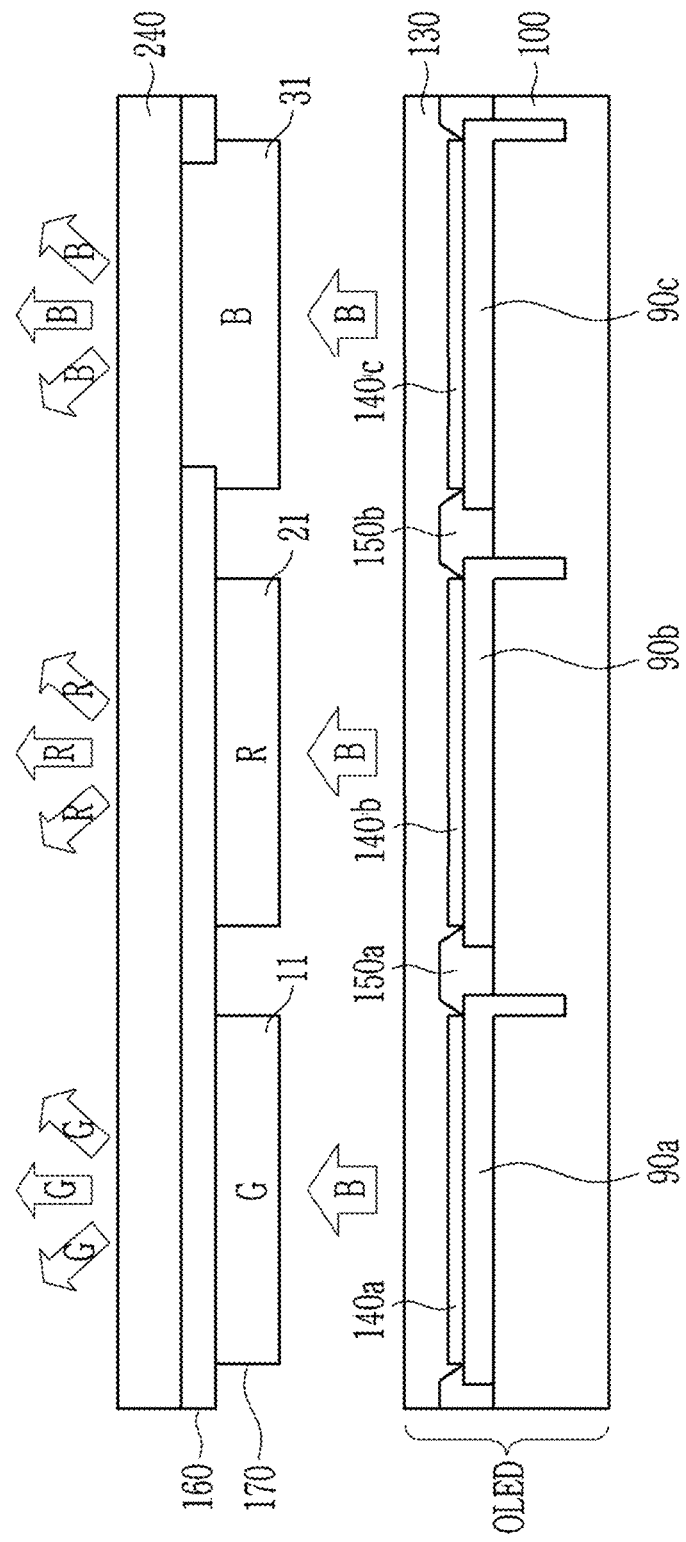
FIG. 5A is a cross-sectional view of a device according to an exemplary embodiment.
Figure 5B:
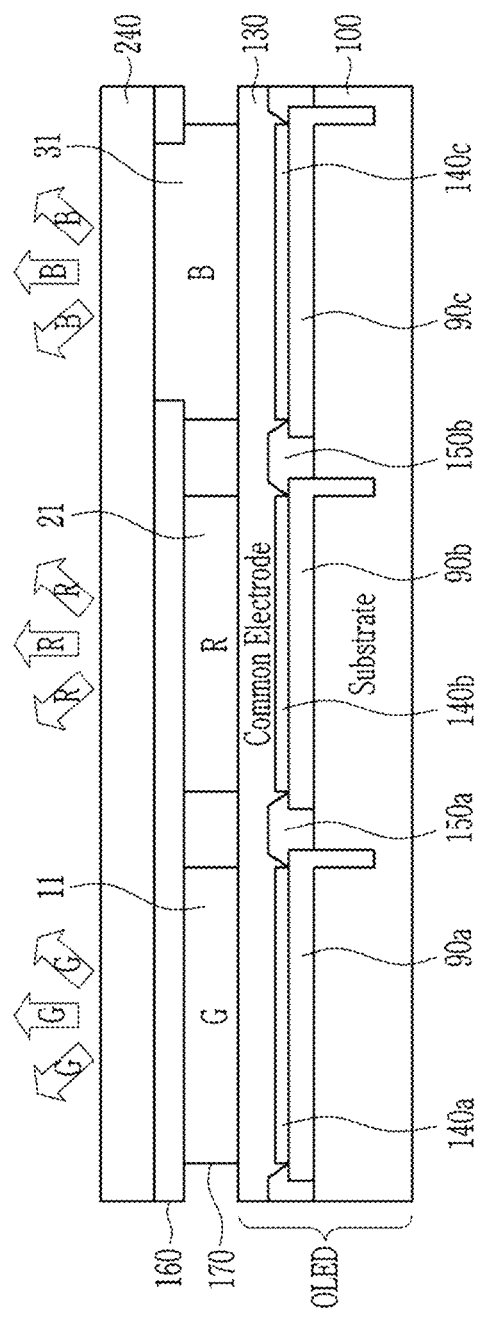
FIG. 5B is a cross-sectional view of a device according to another exemplary embodiment.

FIG. 5A and FIG. 5B show a schematic cross-sectional view of a display of an embodiment of a layered structure. Referring to FIG. 5A and FIG. 5B, the light source may include an organic light emitting diode OLED. For example, the OLED may emit blue light or a light having a wavelength in a region of about 500 nm or less. The organic light emitting diode OLED may include (at least two) pixel electrodes 90a, 90b, 90c formed on a substrate 100, a pixel defining layer 150a, 150b formed between the adjacent pixel electrodes 90a, 90b, 90c, an organic light emitting layer 140a, 140b, 140c formed on the pixel electrodes 90a, 90b, 90c, and a common electrode layer 130 formed on the organic light emitting layer 140a, 140b, 140c.

A thin film transistor and a substrate may be disposed under the organic light emitting diode. The pixel areas of the OLED may be disposed corresponding to the first, second, and third sections that will be described in detail below, respectively.

The stacked structure that includes a quantum dot-polymer composite pattern (e.g., including a first repeating section including green light emitting quantum dots and/or a second repeating section including red light emitting quantum dots) and a substrate, or the quantum dot-polymer composite pattern, may be disposed on or over a light source, for example, directly on the light source.

The light (e.g., blue light) emitted from the light source may enter the second section 21 and the first section 11 of the pattern to emit (e.g., converted) red light R and green light G, respectively. The blue light B emitted from the light source passes through or transmits from the third section 31. Over the second section 21 emitting red light and/or the first section 11 emitting green light, an optical element 160 may be disposed. The optical element may be a blue cut layer which cuts (e.g., reflects or absorbs) blue light and optionally green light, or a first optical filter. The blue cut layer 160 may be disposed on the upper substrate 240. The blue cut layer 160 may be disposed between the upper substrate 240 and the quantum dot-polymer composite pattern and over the first section 11 and the second section 21. Details of the blue cut layer are the same as set forth for the first optical filter 310 below.

The aforementioned device may be fabricated by separately preparing the layered structure and the OLED (for example, the blue OLED), respectively, and combining them. Alternatively, the device may be fabricated by directly forming the pattern of the quantum dot-polymer composite over the OLED.

In another embodiment, the display device may further include a lower substrate 210, an optical element (e.g., polarizer) 300 disposed below the lower substrate 210, and a liquid crystal layer 220 interposed between the layered structure and the lower substrate 210. The layered structure may be disposed in such a manner that a light emitting layer (i.e., the quantum dot-polymer composite pattern) faces the liquid crystal layer. The display device may further include an optical element (e.g., polarizer) 300 between the liquid crystal layer 220 and the light emitting layer. The light source may further include an LED and optionally a light guide panel.

Figure 6:
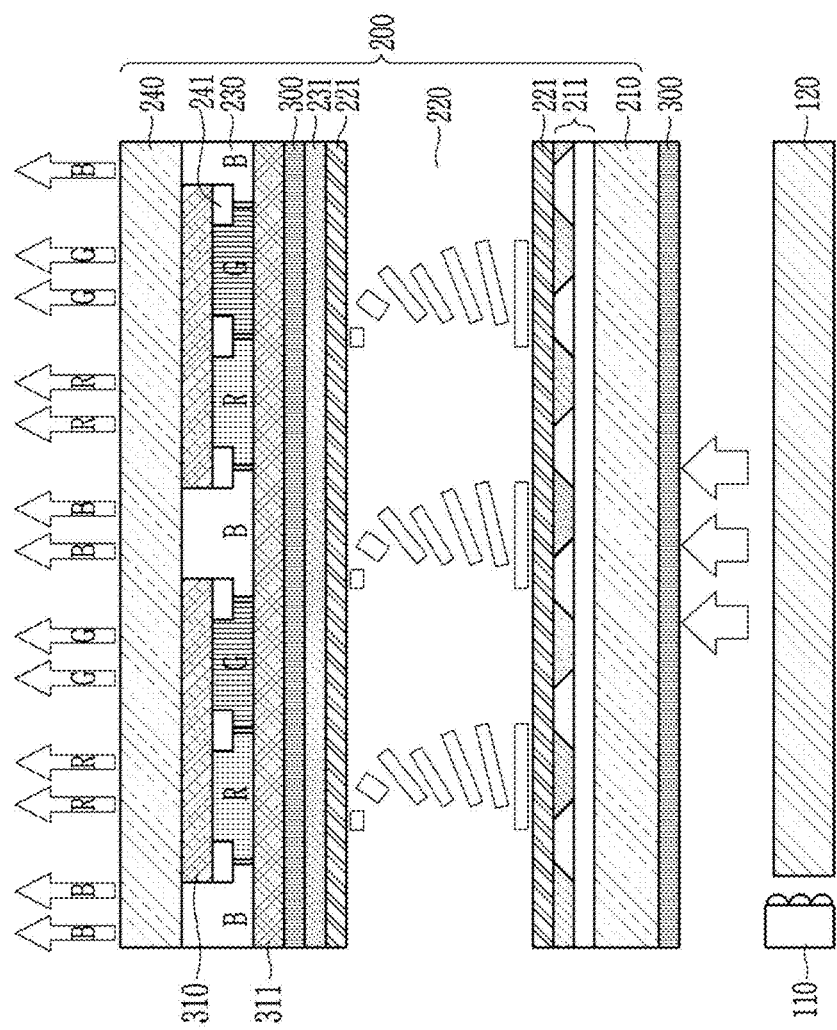
FIG. 6 is a cross-sectional view of a device according to yet another exemplary embodiment.

Referring to FIG. 6, in a non-limiting embodiment, the display device includes a liquid crystal panel 200, an optical element 300 (e.g., polarizer) disposed on and/or under the liquid crystal panel 200, and a backlight unit including a blue light emitting light source 110 under a lower optical element 300. The backlight unit may include a light source 110 and a light guide 120 (edge type). Alternatively, the backlight unit may be a direct light source without a light guide panel (not shown). The liquid crystal panel 200 may include a lower substrate 210, an upper substrate 240, and a liquid crystal layer 220 between the upper and lower substrates, and a light emitting layer (color filter layer) 230 disposed on or under the upper substrate 240. The light emitting layer 230 may include the quantum dot-polymer composite (or a pattern thereof).

A wire plate 211 is provided on an internal surface, for example, on the upper surface of the lower substrate 210. The wire plate 211 may include a plurality of gate wires (not shown) and data wires (not shown) that define a pixel area, a thin film transistor disposed adjacent to a crossing region of gate wires and data wires, and a pixel electrode for each pixel area, but is not limited thereto. Details of such a wire plate are known and are not particularly limited.

The liquid crystal layer 220 may be disposed on the wire plate 211. The liquid crystal layer 220 may include an alignment layer 221 on an upper surface of the liquid crystal layer 220 and on a lower surface of the liquid crystal layer 220, to initially align the liquid crystal material included therein. Details regarding a liquid crystal material, an alignment layer material, a method of forming an alignment layer, a method of forming a liquid crystal layer, a thickness of liquid crystal layer, or the like are known and are not particularly limited.

In an embodiment, an upper optical element or an upper polarizer 300 may be provided between the liquid crystal layer 220 and the upper substrate 240, but it is not limited thereto. For example, the upper optical element or polarizer 300 may be disposed between the liquid crystal layer 220 (or a common electrode 231) and the light emitting layer (or the quantum dot-polymer composite pattern). A black matrix 241 may be provided under the upper substrate 240 (e.g., on a lower surface thereof). Openings within the black matrix 241 are aligned with (or provided to hide) a gate line, a data line, and a thin film transistor of a wire plate 211 on the lower substrate 210. A second section (R) including a color filter emitting red light, a first section (G) including a color filter emitting green light and/or a third section (B) including a color filter for emitting or transmitting blue light may be disposed in the openings within the black matrix 241 (BM). For example, the black matrix 241 may have a lattice shape. If desired, the light emitting layer may further include at least one of a fourth repeating section. The fourth section may be configured to emit light having a color (e.g., cyan, magenta, yellow, or the like) different from the colors of the light emitted from the first to third sections.

The light emitting layer (color filter layer) 230 may be on a transparent common electrode 231.

If desired, the display device may further include a blue cut filter, hereinafter, also referred to as a first optical filter layer. The first optical filter layer 310 may be disposed between upper surfaces of the second section (R) and the first section (G) and the lower surface of the upper substrate 240, or on an upper surface of the upper substrate (240). The first optical filter layer 310 may include a sheet having openings that correspond to the third section (B) (e.g., a pixel area showing, e.g., emitting, a blue color) and may be formed on portions corresponding to the first and second sections (G, R). The first optical filter layer 310 may be formed as a single body structure over the portions of the light emitting layer 230 corresponding to the first and second sections (G, R), and which are other than the portions overlapping the third section, but is not limited thereto. Alternatively, at least two first optical filter layers may be spaced apart from each other and may be disposed over each of the portions overlapping the first and the second sections, respectively.

For example, the first optical filter layer may block light having a predetermined wavelength range in the visible light range and may transmit light having another wavelength range. For example, the first optical filter layer may block blue light and transmit light other than blue light. For example, the first optical filter layer may transmit green light, red light, or yellow light (e.g., the mixed light of the green light and the red light).

The first optical filter layer may include a polymer thin film including a dye and/or a pigment that absorbs light having a specific wavelength, i.e., the wavelength to be blocked. The first optical filter layer may block at least 80%, or at least 90%, even at least 95% of blue light having a wavelength of less than or equal to about 480 nm. With respect to the visible light having other wavelengths, the first optical filter layer may have a light transmittance of greater than or equal to about 70%, for example, greater than or equal to about 80%, greater than or equal to about 90%, or even up to 100%.

The first optical filter layer may absorb and substantially block blue light having a wavelength of less than or equal to about 500 nm, and for example, may selectively transmit green light or red light. In this case, at least two first optical filter layers may be spaced apart and disposed on each of the portions overlapping the first and second sections, respectively. For example, the first optical filter layer selectively transmitting red light may be disposed on the portion overlapping the section emitting red light and the first optical filter layer selectively transmitting green light may be disposed on the portion overlapping the section emitting green light.

In an embodiment, the first optical filter layer may include at least one of a first region and a second region. The first region of the first optical filter layer blocks (e.g., absorbs) blue light and red light and transmits light having a wavelength of a predetermined range, e.g., a wavelength greater than or equal to about 500 nm, greater than or equal to about 510 nm, or greater than or equal to about 515 nm, and less than or equal to about 550 nm, less than or equal to about 540 nm, less than or equal to about 535 nm, less than or equal to about 530 nm, less than or equal to about 525 nm, or less than or equal to about 520 nm. The second region of the first optical filter layer blocks (e.g., absorb) blue light and green light and transmits light having a wavelength of a predetermined range, e.g., a wavelength of greater than or equal to about 600 nm, greater than or equal to about 610 nm, or greater than or equal to about 615 nm and less than or equal to about 650 nm, less than or equal to about 640 nm, less than or equal to about 635 nm, less than or equal to about 630 nm, less than or equal to about 625 nm, or less than or equal to about 620 nm. The first region of the first optical filter layer may be disposed (directly) on or over a location overlapping a green light emitting section and the second region of the first optical filter layer may be disposed (directly) on or over a location overlapping a red light emitting section. The first region and the second region may be optically isolated from one another, for example, by a black matrix. The first optical filter layer may contribute to improving the color purity of a display device.

The first optical filter layer may be a reflection type filter including a plurality of layers (e.g., inorganic material layers) each having a different refractive index. For example, in the first optical filter layer, two layers having different refractive indices may be alternately stacked on each other. For example, a layer having a high refractive index and a layer having a low refractive index may be alternately laminated with each other.

The display device may further include a second optical filter layer 311 (e.g., red/green light or yellow light recycling layer) that is disposed between the light emitting layer 230 and the liquid crystal layer 220, and between the light emitting layer 230—(e.g., the quantum dot polymer composite layer) and the upper polarizer 300. The second optical filter layer 311 may transmit at least a portion of a third light, and reflect at least a portion of a first light and/or a second light. The second optical filter layer may reflect light having a wavelength of greater than 500 nm. The first light may be green (or red) light, the second light may be red (or green) light, and the third light may be blue light.

Another embodiment provides an electronic device including the quantum dot. The device may include a light emitting diode (LED), an organic light emitting diode (OLED), a sensor, a solar cell, an imaging sensor, or a liquid crystal display (LCD), but is not limited thereto.

Hereinafter, the embodiments are illustrated in more detail with reference to examples. However, the present disclosure is not limited thereto.

EXAMPLES

Analysis Method

[1] UV-Visible Absorption Analysis

An Agilent Cary5000 spectrometer is used to perform a UV spectroscopy analysis and UV-Visible absorption spectrum is obtained.

[2] Photoluminescence Analysis

Photoluminescence Analysis is made by using Hitachi F-7000 spectrometer and a photoluminescence spectrum is obtained.

[3] Quantum Yield (QY) of the Quantum Dot

A quantum yield is obtained by dividing the number of the photons emitted from the sample by the number of the photons absorbed by the sample. It is measured by using QE-2100 (manufactured by Otsuka electronics Co., Ltd.) with respect to a quantum dot containing dispersion or a quantum dot polymer composite.

[4] Blue Light Absorption Rate and Conversion Efficiency of the Composite

Using an integrating sphere, a light dose of the blue excitation light (B) is measured. Then, a quantum dot polymer composite is placed in the integrating sphere and is irradiated with the bluet excitation light. A light dose of green (or red) light emitted from the composite (A) and a light dose of blue light passing through the composite (B') are measured. From the measured values, a blue light absorption rate and the photoconversion efficiency are calculated by the following equations:

Quantum efficiency (QE) of the composite=$A/B$ blue light absorption rate=$(B-B')/B$ photoconversion efficiency=$A/(B-B')$

[5] TEM Analysis

A transmission electron microscopic (TEM) analysis is performed using Titan ChemiSTEM electron microscope.

[6] ICP Analysis

An inductively coupled plasma-atomic emission spectroscopy (ICP-AES) analysis is performed using Shimadzu ICPS-8100.

Reference Example 1

Indium acetate and palmitic acid are dissolved in 1-octadecene in a 200 milliliter (mL) reaction flask, subjected to a vacuum state at 120° C. for one hour. A mole ratio of indium to palmitic acid is 1:3. The atmosphere in the flask is exchanged with $N_2$. After the reaction flask is heated to 300° C., a mixed solution of tris(trimethylsilyl)phosphine ($TMS_3P$) and trioctylphosphine (TOP) is quickly injected, and the reaction proceeds for a predetermined time (e.g., for 20 minutes). The reaction mixture then is rapidly cooled to room temperature and acetone is added thereto to produce nanocrystals, which are then separated by centrifugation and dispersed in toluene to obtain a toluene dispersion of the InP core nanocrystals. The amount of the $TMS_3P$ is about 0.5 moles per one mole of indium. A size of the InP core thus obtained is about 2.2 nm.

Example 1

Selenium and sulfur are dispersed in trioctylphosphine (TOP) to obtain a Se/TOP stock solution and a S/TOP stock solution, respectively.

In a 200 mL reaction flask, zinc acetate and oleic acid are dissolved in trioctyl amine and the solution is subjected to vacuum at 120° C. for 10 minutes. The atmosphere in the flask is replaced with $N_2$ while the oleyl amine is added thereto. While the resulting solution is heated to about 320° C., a toluene dispersion of the InP semiconductor nanocrystal core are injected thereto and a predetermined amount of Se/TOP stock solution is injected into the reaction flask over three times. A reaction is carried out to obtain a reaction solution including a particle having a ZnSe shell disposed on the InP core. A total of reaction time is 90 minutes.

Then, at the aforementioned reaction temperature, the S/TOP stock solution and the zinc acetate are injected to the reaction mixture. A reaction is carried out to obtain a resulting solution including a particle having a ZnS based shell disposed on the ZnSe shell. A total of reaction time is 70 minutes.

The amounts of Se, S, and Zn used in this example are 16, 12, and 50 per 1 mole of Indium, respectively.

An excess amount of ethanol is added to the final reaction mixture including the resulting core/multishell quantum dot, which is then centrifuged. After centrifugation, the supernatant is discarded, and the precipitate is dried and dispersed in chloroform to obtain a quantum dot solution (hereinafter, QD solution).

For the obtained QD solution, a ICP-AES analysis is made, and the results are shown in Table 1. A photoluminescence spectroscopic analysis and a TEM analysis are made for the QD solution, and the results are shown in Table 2.

Figure 7A:
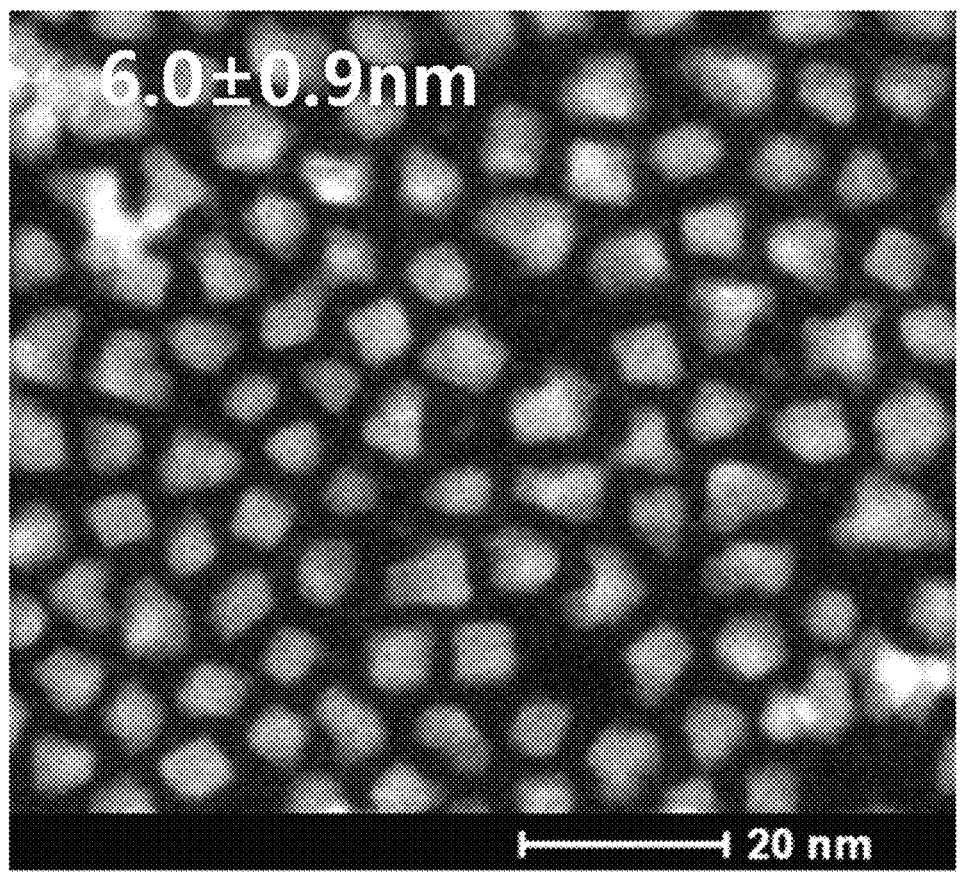
FIG. 7A is a transmission electron microscopic image of the population of quantum dots prepared in Example 1.
Figure 7B:
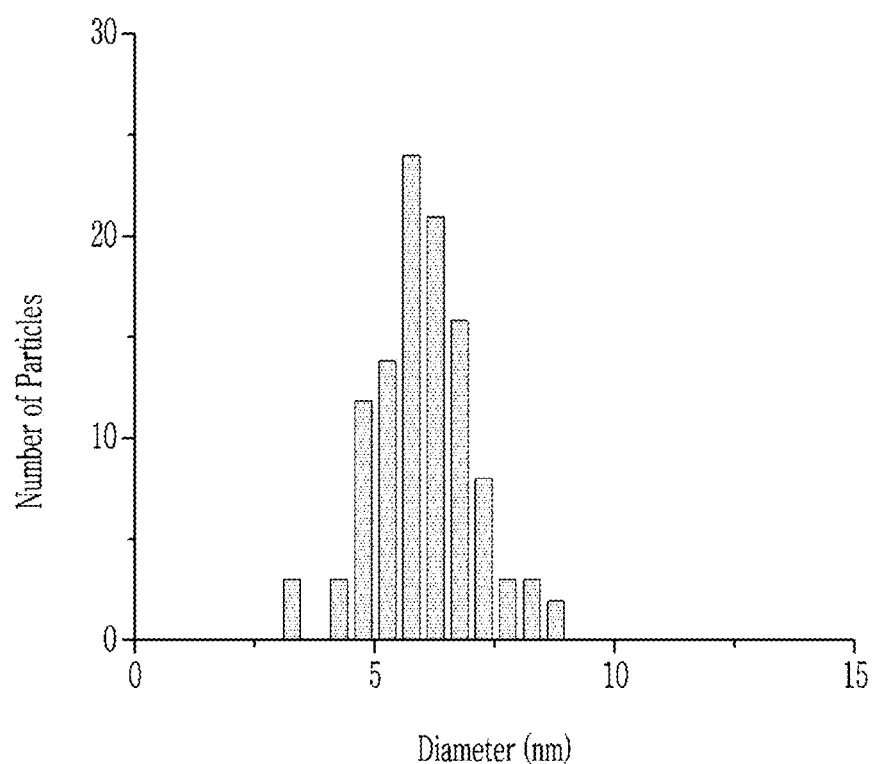
FIG. 7B is a histogram showing a size distribution of the population of quantum dots prepared in Example 1.

A TEM image and a particle size distribution histogram are shown in FIG. 7a and FIG. 7B, respectively.

Comparative Example 1

Selenium and sulfur are dispersed in trioctylphosphine (TOP) to obtain a Se/TOP stock solution and a S/TOP stock solution, respectively.

In a 200 mL reaction flask, zinc acetate and oleic acid are dissolved in trioctyl amine and the solution is subjected to vacuum at 120° C. for 10 minutes. The atmosphere in the flask is replaced with $N_2$. While the resulting solution is heated to about 320° C., a toluene dispersion of the InP semiconductor nanocrystal core is injected thereto and the Se/TOP stock solution, the S/TOP stock solution, and optionally the zinc acetate are injected into the reaction flask over at least three times. A reaction is carried out to obtain a reaction solution including a particle having a ZnSeS shell disposed on the InP core. A total of reaction time is 90 minutes.

Then, at the aforementioned reaction temperature, the S/TOP stock solution and the zinc acetate are injected to the reaction mixture. A reaction is carried out to obtain a resulting solution including a particle having a ZnS based shell disposed on the ZnSeS shell. A total of reaction time is 100 minutes.

The amounts of Se, S, and Zn used in this example are 14, 22, and 50 per 1 mole of Indium, respectively.

An excess amount of ethanol is added to the final reaction mixture including the resulting core/multishell quantum dot, which is then centrifuged. After centrifugation, the supernatant is discarded, and the precipitate is dried and dispersed in chloroform to obtain a quantum dot solution (hereinafter, QD solution).

For the obtained QD solution, a ICP-AES analysis is made and the results are shown in Table 1. A photoluminescence spectroscopic analysis and a TEM analysis are made for the QD solution, and the results are shown in Table 2.

Figure 8A:
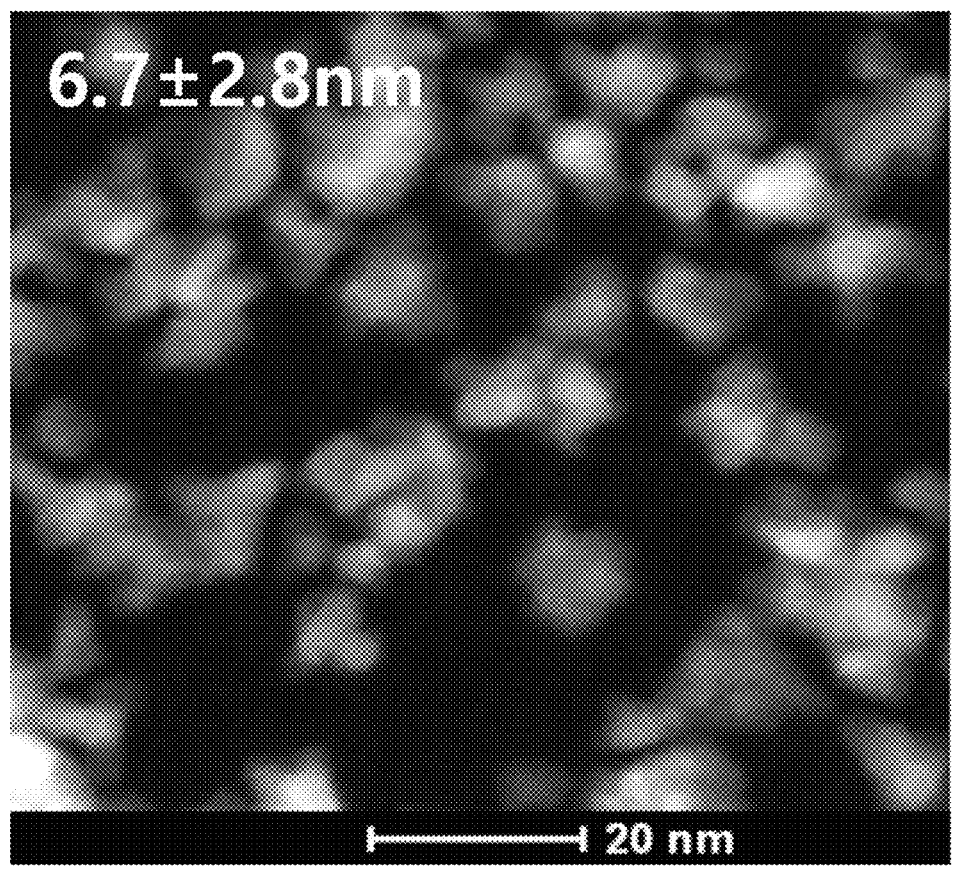
FIG. 8A is a transmission electron microscopic image of the population of quantum dots prepared in Comparative Example 1.
Figure 8B:
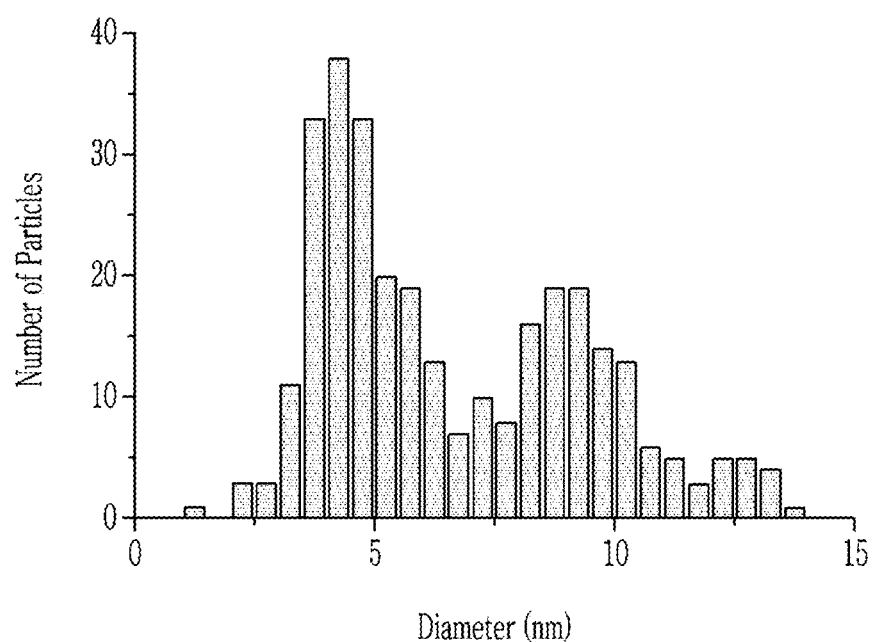
FIG. 8B is a histogram showing a size distribution of the population of quantum dots prepared in Comparative Example 1.

A TEM image and a particle size distribution histogram are shown in FIG. 8a and FIG. 8B, respectively.

Comparative Example 2

A population of core-multishell quantum dots is prepared in the same manner as in Example 1, except that the oleyl amine is not used. A TEM analysis is made for the QD population, and the results are shown in Table 2.

Figure 9A:
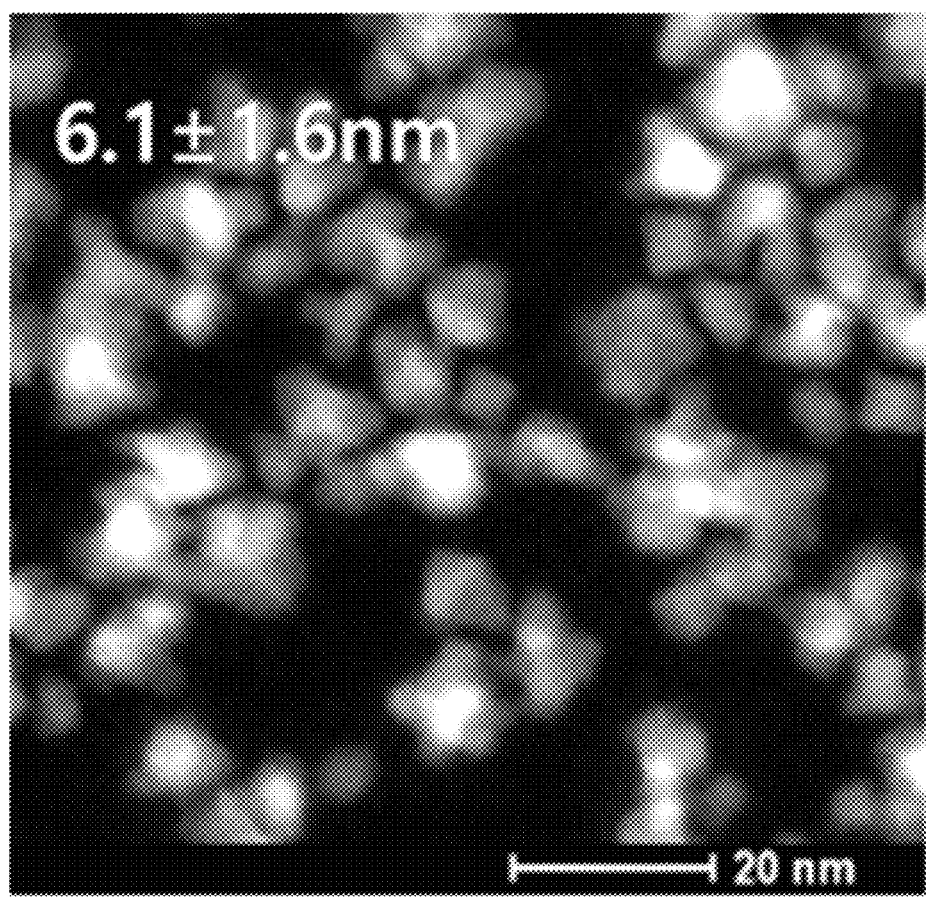
FIG. 9A is a transmission electron microscopic image of the population of quantum dots prepared in Comparative Example 2.
Figure 9B:
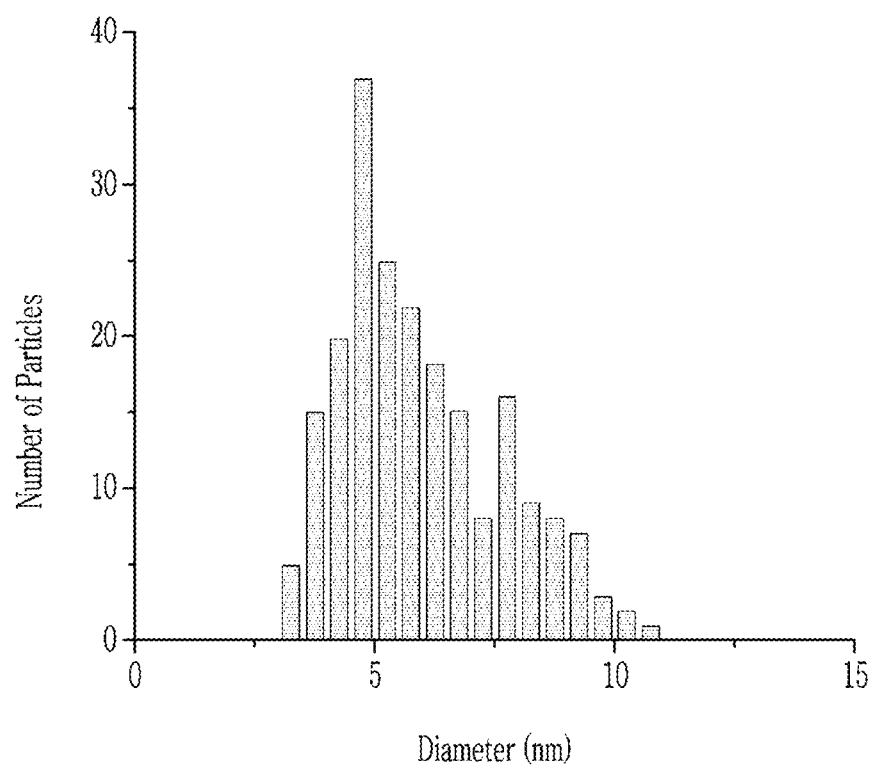
FIG. 9B is a histogram showing a size distribution of the population of quantum dots prepared in Comparative Example 2.

A TEM image and a particle size distribution histogram are shown in FIG. 9a and FIG. 9B, respectively.

TABLE 1

| | Relative mole ratio | | |
|---|---|---|---|
| | S + Se/In | Zn/In | Zn/(Se + S) |
| Comp. Ex 1 | 26 | 31 | 1.19 |
| Ex 1 | 22 | 26 | 1.18 |

TABLE 2

| | solidity | Particle size distribution (SD/Avg. size/) | FWHM (nm) | QY (%) | average Size (nm) | Standard deviation (SD: nm) |
|---|---|---|---|---|---|---|
| Comp. Ex 1 | 0.8 | 42% | 44 | 74 | 6.7 | 2.8 |
| Ex 1 | 0.92 | 15% | 36 | 78 | 6.0 | 0.9 |
| Comp. Ex 2 | 0.82 | over 20% | — | — | 6.1 | 1.6 |

The results of table 2 confirm that the quantum dots of Example 1 have a higher value of solidity and a uniform particle size distribution and exhibit a low level of FWHM and enhanced QY.

Experimental Example: Production of a Quantum Dot Polymer Composite and a Pattern Thereof Each of a chloroform dispersion of the quantum dots of Example 1 and a chloroform dispersion of the quantum dots of Comparative Example 1 is mixed with a solution of a binder polymer, which is a four membered copolymer of methacrylic acid, benzyl methacrylate, hydroxyethyl methacrylate, and styrene, (acid value: 130 milligrams (mg) per gram of KOH (mg KOH/g), molecular weight: 8,000 g/mol, acrylic acid:benzyl methacrylate:hydroxyethyl methacrylate:styrene (molar ratio)=61.5%:12%:16.3%:10.2%) (solvent: propylene glycol monomethyl ether acetate, PGMEA, a concentration of 30 percent by weight, wt %) to form a quantum dot-binder dispersion.

To the quantum dot-binder dispersion prepared above, a hexaacrylate having the following structure (as a photopolymerizable monomer), ethylene glycol di-3-mercaptopropionate (hereinafter, 2T, as a multi-thiol compound), an oxime ester compound (as an initiator), $TiO_2$ as a metal oxide fine particle, and PGMEA (as a solvent) are added to obtain a composition.

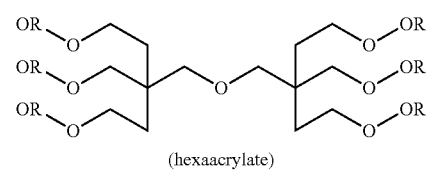

(hexaacrylate)

wherein

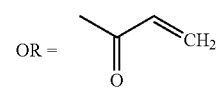

Based on a total solid content, the prepared composition includes 40 wt % of quantum dots, 12.5 wt % of the binder polymer, 25 wt % of 2T, 12 wt % of the photopolymerizable monomer, 0.5 wt % of the photoinitiator, and 10 wt % of the metal oxide fine particle. The total solid content is about 25%.

The composition obtained above is spin-coated on a glass substrate at 150 revolutions per minute (rpm) for 5 seconds (s) to provide a film. The obtained film is pre-baked at 100° C. (PRB). The pre-baked film is exposed to light (wavelength: 365 nanometers (nm), intensity: 100 millijoules, mJ) under a mask having a predetermined pattern (e.g., a square dot or stripe pattern) for 1 s (EXP) and developed with a potassium hydroxide aqueous solution (conc.: 0.043%) for 50 seconds to obtain a pattern of a quantum dot polymer composite (thickness: 6 μm).

The obtained pattern is heat-treated at a temperature of 180° C. for 30 minutes under a nitrogen atmosphere. (POB)

For the obtained pattern film, a blue light absorption rate and a quantum efficiency after POB are measured and the results are shown in Table 3.

TABLE 3

| | Blue light absorption rate (%) | QE (%) after POB |
|---|---|---|
| Comp. Example 1 | 92 | 31 |
| Example 1 | 84 | 26 |

The results of Table 3 confirm that a quantum dot polymer composite pattern including the quantum dots of Example 1 exhibit a higher blue light absorption rate and a higher quantum efficiency.

The quantum dot polymer composite including the QD of Example 1 may exhibit a process maintenance ratio of greater than or equal to about 95% as determined by a ratio of the Quantum efficiency of the composite after POB with respect to QE before POB.

While this disclosure has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A quantum dot population comprising a plurality of cadmium free quantum dots, wherein
   the plurality of cadmium free quantum dots comprises
   a semiconductor nanocrystal core comprising indium (In) and phosphorous (P),
   a first semiconductor nanocrystal shell disposed on the semiconductor nanocrystal core and comprising zinc and selenium, and
   a second semiconductor nanocrystal shell disposed on the first semiconductor nanocrystal shell and comprising zinc and sulfur,
   wherein an average particle size of the plurality of cadmium free quantum dots is greater than or equal to about 5.5 nanometers,
   a standard deviation of particle sizes of the plurality of cadmium free quantum dots is less than or equal to about 20% of the average particle size, and
   an average solidity of the plurality of cadmium free quantum dots is greater than or equal to about 0.85.

2. The quantum dot population of claim 1, wherein the plurality of cadmium free quantum dots comprises an organic ligand on surfaces thereof, and the organic ligand comprises a carboxylic acid compound and a primary amine compound.

3. The quantum dot population of claim 2, wherein the carboxylic acid compound comprises a C5 to C30 aliphatic hydrocarbon group, and a primary amine group of the primary amine compound comprises a C5 to C30 aliphatic hydrocarbon group.

4. The quantum dot population of claim 3, wherein the primary amine group has a C5 to C30 alkenyl group.

5. The quantum dot population of claim 1, wherein the plurality of cadmium free quantum dots do not comprise boron.

6. The quantum dot population of claim 1, wherein the first semiconductor nanocrystal shell is disposed directly on the semiconductor nanocrystal core.

7. The quantum dot population of claim 1, wherein the first semiconductor nanocrystal shell does not comprise sulfur.

8. The quantum dot population of claim 1, wherein the first semiconductor nanocrystal shell has a thickness of greater than or equal to about 3 monolayers and less than or equal to about 10 monolayers.

9. The quantum dot population of claim 1, wherein the second semiconductor nanocrystal shell is an outermost layer of the cadmium free quantum dot.

10. The quantum dot population of claim 1, wherein the second semiconductor nanocrystal shell is disposed directly on the surface of the first semiconductor nanocrystal shell.

11. The quantum dot population of claim 1, wherein the average particle size of the plurality of the cadmium free quantum dots is greater than or equal to about 5.8 nanometers and the standard deviation of particle sizes of the plurality of cadmium free quantum dots is less than or equal to about 18% of the average particle size.

12. The quantum dot population of claim 1, wherein the average solidity of the plurality of cadmium free quantum dots is greater than or equal to about 0.90.

13. The quantum dot population of claim 1, wherein a maximum photoluminescent peak of the cadmium free quantum dots has a full width at half maximum of less than or equal to about 40 nanometers.

14. The quantum dot population of claim 1, wherein a quantum efficiency of the plurality of cadmium free quantum dots is greater than or equal to about 70%.

15. A method of producing the quantum dot population of claim 1, which comprises:
   reacting a zinc containing precursor and a selenium containing precursor in the presence of a semiconductor nanocrystal core particle including indium and phosphorous in a heated organic solvent and an organic ligand at a first reaction temperature to form a first semiconductor nanocrystal shell on the semiconductor nanocrystal core; and
   reacting a zinc containing precursor and a sulfur containing precursor in the presence of a particle having the first semiconductor nanocrystal shell formed on the core in the organic solvent and the organic ligand at a second reaction temperature to form a second semiconductor nanocrystal shell on the first semiconductor nanocrystal shell, wherein the organic ligand includes a carboxylic acid compound and a primary amine compound.

16. The method of claim 15, wherein the method does not comprise lowering a temperature of a reaction mixture including the particle having the first semiconductor nanocrystal shell on the core to a temperature below about 100° C.

17. A quantum dot-polymer composite comprising:
a polymer matrix; and
a quantum dot population of claim 1, wherein the plurality of cadmium free quantum dots are dispersed in the polymer matrix.

18. The quantum dot-polymer composite of claim 17, wherein the polymer matrix comprises a crosslinked polymer, a binder polymer having a carboxylic acid group, or a combination thereof.

19. The quantum dot-polymer composite of claim 18, wherein the crosslinked polymer comprises a polymerization product of a photopolymerizable monomer including at least carbon-carbon double bond, a polymerization product of the photopolymerizable monomer and a multi-thiol compound having at least two thiol groups at its terminal end, or a combination thereof.

20. The quantum dot-polymer composite of claim 17, wherein the quantum dot polymer composite comprises a plurality of metal oxide fine particles in the polymer matrix.

21. The quantum dot-polymer composite of claim 17, wherein a blue light absorption rate of the quantum dot-polymer composite with respect to light having a wavelength of 450 nanometers is greater than or equal to about 88% when an amount of the cadmium free quantum dot is about 45% based on a total weight of the composite.

22. The quantum dot-polymer composite of claim 17, wherein the quantum dot-polymer composite is configured to exhibit a maximum photoluminescent peak with a full width at half maximum of less than or equal to about 40 nanometers.

23. A display device, which comprises
a light source and a light emitting element,
wherein the light emitting element comprises the quantum dot-polymer composite of claim 17 and the light source is configured to provide the light emitting element with incident light.

24. The display device of claim 23, wherein the incident light has a luminescence peak wavelength of about 440 nanometers to about 460 nanometers.

25. The display device of claim 23, wherein, the light emitting element comprises a sheet comprising the quantum dot polymer composite.

26. The display device of claim 23, wherein the light emitting element comprises a stacked structure including a substrate and a light emitting layer disposed on the substrate, wherein the light emitting layer includes a pattern of the quantum dot polymer composite and the pattern comprises at least one repeating section configured to emit light at a predetermined wavelength.

27. The display device of claim 23, wherein the display device is configured to have a color reproducibility of greater than or equal to about 80% measured in accordance with a BT 2020 standard.

* * * * *